(12) United States Patent
DiSilvestro et al.

(10) Patent No.: US 11,068,822 B2
(45) Date of Patent: Jul. 20, 2021

(54) SYSTEM AND METHOD FOR PERFORMING A COMPUTER ASSISTED ORTHOPAEDIC SURGICAL PROCEDURE

(71) Applicant: DEPUY SYNTHES PRODUCTS, INC., Raynham, MA (US)

(72) Inventors: Mark R. DiSilvestro, Columbia City, IN (US); Jason T. Sherman, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 500 days.

(21) Appl. No.: 15/800,141

(22) Filed: Nov. 1, 2017

(65) Prior Publication Data

US 2018/0130001 A1     May 10, 2018

Related U.S. Application Data

(63) Continuation of application No. 15/082,000, filed on Mar. 28, 2016, which is a continuation of application
(Continued)

(51) Int. Cl.
*G06Q 10/06*     (2012.01)
*G06F 16/51*     (2019.01)
(Continued)

(52) U.S. Cl.
CPC ....... *G06Q 10/06316* (2013.01); *G06F 16/51* (2019.01); *G06F 16/532* (2019.01);
(Continued)

(58) Field of Classification Search
CPC ............ G06Q 50/22; G06Q 10/06316; G06Q 10/087; G06H 20/40; G06H 50/20;
(Continued)

(56) References Cited

U.S. PATENT DOCUMENTS

| 4,501,266 A | 2/1985 | McDaniel |
| 4,791,934 A | 12/1988 | Brunnett |

(Continued)

FOREIGN PATENT DOCUMENTS

| DE | 10335410 A1 | 2/2005 |
| EP | 0720834 B1 | 6/1999 |

(Continued)

OTHER PUBLICATIONS

Taylor et al., Computer-Integrated Surgery and Medical Robotics, Jul. 15, 2001, The Johns Hopkins University and The Hebrew University of Jerusalem, pp. 1-44, https://www.cs.huji.ac.il/labs/casmip/wp-content/uploads/2015/08/b02-2002-09-cisrobots.pdf (Year: 2001).*

(Continued)

*Primary Examiner* — Joy Chng
(74) *Attorney, Agent, or Firm* — Barnes & Thornburg LLP

(57) ABSTRACT

A computer assisted surgery system includes a controller configured to display images of the surgical procedure according to a workflow plan. The controller is configured to retrieve data and determine the workflow plan based on the data. The controller may also be configured to record and store data related to the surgical procedure on, for example, a hospital network.

9 Claims, 21 Drawing Sheets

Related U.S. Application Data

No. 14/104,216, filed on Dec. 12, 2013, now Pat. No. 9,299,117, which is a continuation of application No. 11/420,244, filed on May 25, 2006, now Pat. No. 8,635,082.

(51) Int. Cl.

| | | |
|---|---|---|
| *G06F 16/532* | (2019.01) | |
| *G06F 16/58* | (2019.01) | |
| *G16H 10/60* | (2018.01) | |
| *G16H 40/20* | (2018.01) | |
| *G06Q 10/08* | (2012.01) | |
| *G16H 20/40* | (2018.01) | |
| *G16H 30/20* | (2018.01) | |
| *G16H 50/20* | (2018.01) | |
| *A61F 2/30* | (2006.01) | |

(52) U.S. Cl.
 CPC ....... *G06F 16/5866* (2019.01); *G06Q 10/087* (2013.01); *G16H 10/60* (2018.01); *G16H 20/40* (2018.01); *G16H 30/20* (2018.01); *G16H 40/20* (2018.01); *G16H 50/20* (2018.01); *A61F 2002/30953* (2013.01)

(58) Field of Classification Search
 CPC ........ G16H 20/40; G16H 40/20; G16H 10/60; G16H 30/20; G16H 50/20; A61F 2002/30953; G06F 16/51; G06F 16/5866; G06F 16/532
 USPC .......................................................... 705/2–3
 See application file for complete search history.

(56) References Cited

U.S. PATENT DOCUMENTS

| | | | |
|---|---|---|---|
| 4,899,761 A | 2/1990 | Brown et al. | |
| 4,973,331 A | 11/1990 | Pursley et al. | |
| 5,082,003 A | 1/1992 | Lamb et al. | |
| 5,197,488 A | 3/1993 | Kovacevic | |
| 5,211,165 A | 5/1993 | Dumoulin et al. | |
| 5,213,112 A | 5/1993 | Niwa et al. | |
| 5,251,635 A | 10/1993 | Dumoulin et al. | |
| 5,255,680 A | 10/1993 | Darrow et al. | |
| 5,265,610 A | 11/1993 | Darrow et al. | |
| 5,305,244 A | 4/1994 | Newman et al. | |
| 5,329,933 A | 7/1994 | Graf | |
| 5,360,016 A | 11/1994 | Kovacevic | |
| 5,383,454 A | 1/1995 | Bucholz | |
| 5,470,354 A | 11/1995 | Hershberger et al. | |
| 5,526,812 A | 6/1996 | Dumoulin et al. | |
| 5,540,696 A | 7/1996 | Booth, Jr. et al. | |
| 5,682,886 A * | 11/1997 | Delp ................... A61B 17/154 128/920 | |
| 5,688,280 A | 11/1997 | Booth, Jr. et al. | |
| 5,711,299 A | 1/1998 | Manwaring et al. | |
| 5,719,743 A | 2/1998 | Jenkins et al. | |
| 5,719,744 A | 2/1998 | Jenkins et al. | |
| 5,733,292 A | 3/1998 | Gustilo et al. | |
| 5,757,339 A | 5/1998 | Williams et al. | |
| 5,799,099 A | 8/1998 | Wang et al. | |
| 5,824,085 A | 10/1998 | Sahay et al. | |
| 5,844,656 A | 12/1998 | Ronzani et al. | |
| 5,844,824 A | 12/1998 | Newman et al. | |
| 5,967,980 A | 10/1999 | Ferre et al. | |
| 6,022,377 A | 2/2000 | Nuelle et al. | |
| 6,034,296 A | 3/2000 | Elvin et al. | |
| 6,146,390 A | 11/2000 | Heilbrun et al. | |
| 6,165,181 A | 12/2000 | Heilbrun et al. | |
| 6,167,145 A | 12/2000 | Foley et al. | |
| 6,241,671 B1 | 6/2001 | Ritter et al. | |
| 6,246,900 B1 | 6/2001 | Cosman et al. | |
| 6,285,902 B1 | 9/2001 | Kienzle, III et al. | |
| 6,301,593 B1 | 10/2001 | Toyosato | |
| 6,314,310 B1 | 11/2001 | Ben-Haim et al. | |
| 6,341,231 B1 | 1/2002 | Ferre et al. | |
| 6,351,659 B1 | 2/2002 | Vilsmeier | |
| 6,370,224 B1 | 4/2002 | Simon et al. | |
| 6,405,072 B1 | 6/2002 | Cosman | |
| 6,421,232 B2 | 7/2002 | Sallam | |
| 6,424,856 B1 | 7/2002 | Vilsmeier et al. | |
| 6,430,434 B1 | 8/2002 | Mittelstadt | |
| 6,434,415 B1 | 8/2002 | Foley et al. | |
| 6,442,416 B1 | 8/2002 | Schultz | |
| 6,445,943 B1 | 9/2002 | Ferre et al. | |
| 6,447,448 B1 | 9/2002 | Ishikawa et al. | |
| 6,463,361 B1 | 10/2002 | Wang et al. | |
| 6,474,341 B1 | 11/2002 | Hunter et al. | |
| 6,490,467 B1 | 12/2002 | Bucholz et al. | |
| 6,491,702 B2 | 12/2002 | Heilbrun et al. | |
| 6,493,573 B1 | 12/2002 | Martinelli et al. | |
| 6,496,099 B2 | 12/2002 | Wang et al. | |
| 6,499,488 B1 | 12/2002 | Hunter et al. | |
| 6,516,212 B1 | 2/2003 | Bladen et al. | |
| 6,532,482 B1 | 3/2003 | Toyosato | |
| 6,535,756 B1 | 3/2003 | Simon et al. | |
| 6,546,279 B1 | 4/2003 | Bova et al. | |
| 6,552,899 B2 | 4/2003 | Ronzani et al. | |
| 6,584,174 B2 | 6/2003 | Schubert et al. | |
| 6,625,563 B2 | 9/2003 | Kirsch et al. | |
| 6,633,773 B1 | 10/2003 | Reisfeld | |
| 6,640,127 B1 | 10/2003 | Kosaka et al. | |
| 6,642,836 B1 | 11/2003 | Wang et al. | |
| 6,646,541 B1 | 11/2003 | Wang et al. | |
| 6,648,896 B2 | 11/2003 | Overes et al. | |
| 6,662,036 B2 | 12/2003 | Cosman | |
| 6,687,531 B1 | 2/2004 | Ferre et al. | |
| 6,692,448 B2 | 2/2004 | Tanaka et al. | |
| 6,701,174 B1 | 3/2004 | Krause et al. | |
| 6,711,432 B1 | 3/2004 | Krause et al. | |
| 6,724,922 B1 | 4/2004 | Vilsmeier | |
| 6,725,080 B2 | 4/2004 | Melkent et al. | |
| 6,738,656 B1 | 5/2004 | Ferre et al. | |
| 6,758,850 B2 | 7/2004 | Smith et al. | |
| 6,786,930 B2 | 9/2004 | Biscup | |
| 6,798,391 B2 | 9/2004 | Peterson | |
| 6,847,336 B1 | 1/2005 | Lemelson et al. | |
| 6,859,660 B2 | 2/2005 | Vilsmeier | |
| 6,859,661 B2 * | 2/2005 | Tuke ................... A61B 90/36 600/424 | |
| 6,873,867 B2 | 3/2005 | Vilsmeier | |
| 6,892,090 B2 | 5/2005 | Verard et al. | |
| 6,920,347 B2 | 7/2005 | Simon et al. | |
| 6,925,447 B2 | 8/2005 | McMenimen et al. | |
| 6,934,575 B2 | 8/2005 | Ferre et al. | |
| 6,947,786 B2 | 9/2005 | Simon et al. | |
| 6,968,846 B2 | 11/2005 | Viswanathan | |
| 6,978,166 B2 | 12/2005 | Foley et al. | |
| 7,153,281 B2 | 12/2006 | Holmes | |
| 7,340,316 B2 | 3/2008 | Spaeth et al. | |
| 7,578,821 B2 | 8/2009 | Fisher et al. | |
| 7,615,055 B2 | 11/2009 | DiSilvestro | |
| 8,133,229 B1 | 3/2012 | Bonutti | |
| 8,394,104 B2 | 3/2013 | DiSilvestro | |
| 8,635,082 B2 | 1/2014 | Woods et al. | |
| 8,734,454 B2 | 5/2014 | DiSilvestro | |
| 9,299,117 B2 | 3/2016 | Woods et al. | |
| 9,861,446 B2 | 1/2018 | Lang | |
| 10,004,449 B2 | 6/2018 | Stein et al. | |
| 2001/0039421 A1 | 11/2001 | Heilbrun et al. | |
| 2002/0007294 A1 | 1/2002 | Bradbury et al. | |
| 2002/0087062 A1 | 7/2002 | Schmidt et al. | |
| 2002/0095081 A1 | 7/2002 | Vilsmeier | |
| 2002/0128651 A1 | 9/2002 | Hyde, Jr. | |
| 2002/0156480 A1 | 10/2002 | Overes et al. | |
| 2002/0183610 A1 | 12/2002 | Foley et al. | |
| 2002/0188194 A1 | 12/2002 | Cosman | |
| 2002/0196344 A1 | 12/2002 | McIntyre et al. | |
| 2002/0198451 A1 | 12/2002 | Carson | |
| 2003/0088179 A1 | 5/2003 | Seeley et al. | |
| 2003/0144669 A1 | 7/2003 | Robinson | |
| 2003/0153978 A1 | 8/2003 | Whiteside | |
| 2003/0236472 A1 | 12/2003 | Van Hoeck et al. | |

(56) References Cited

U.S. PATENT DOCUMENTS

| | | |
|---|---|---|
| 2004/0030245 A1 | 2/2004 | Noble et al. |
| 2004/0039254 A1 | 2/2004 | Stivoric et al. |
| 2004/0068187 A1 | 4/2004 | Krause et al. |
| 2004/0073279 A1 | 4/2004 | Malackowski et al. |
| 2004/0097951 A1 | 5/2004 | Steffensmeier |
| 2004/0122787 A1 | 6/2004 | Avinash et al. |
| 2004/0122790 A1 | 6/2004 | Walker et al. |
| 2004/0124964 A1 | 7/2004 | Wang et al. |
| 2005/0012617 A1* | 1/2005 | DiSilvestro .............. A61F 2/32 340/572.8 |
| 2005/0038442 A1 | 2/2005 | Freeman |
| 2005/0059873 A1 | 3/2005 | Glozman et al. |
| 2005/0149379 A1 | 7/2005 | Cyr et al. |
| 2005/0177170 A1 | 8/2005 | Fisher et al. |
| 2005/0182315 A1 | 8/2005 | Ritter et al. |
| 2005/0203384 A1* | 9/2005 | Sati ......................... G06F 3/011 600/426 |
| 2005/0228245 A1 | 10/2005 | Quy |
| 2005/0234448 A1 | 10/2005 | McCarthy |
| 2005/0267485 A1 | 12/2005 | Cordes et al. |
| 2006/0020915 A1 | 1/2006 | Lloyd et al. |
| 2006/0241569 A1 | 10/2006 | DiSilvestro |
| 2007/0015999 A1 | 1/2007 | Heldreth et al. |
| 2007/0078678 A1 | 4/2007 | DiSilvestro et al. |
| 2007/0238982 A1* | 10/2007 | Caylor, III ........... A61B 5/1127 600/424 |
| 2008/0269596 A1* | 10/2008 | Revie .................... A61F 2/4603 600/424 |
| 2010/0249790 A1 | 9/2010 | Roche |
| 2010/0249791 A1 | 9/2010 | Roche |
| 2012/0143198 A1 | 6/2012 | Boyer et al. |
| 2013/0226035 A1 | 8/2013 | Stein et al. |
| 2016/0239779 A1 | 8/2016 | DiSilvestro et al. |
| 2016/0331465 A1 | 11/2016 | Kim et al. |

FOREIGN PATENT DOCUMENTS

| | | |
|---|---|---|
| EP | 1020734 A2 | 7/2000 |
| EP | 1321097 A2 | 6/2003 |
| EP | 1348382 A2 | 10/2003 |
| JP | 3284254 A | 12/1991 |
| JP | 11197159 A | 7/1999 |
| JP | 2001137259 A | 5/2001 |
| JP | 2001511691 A | 8/2001 |
| JP | 2002291706 A | 10/2002 |
| JP | 2005518854 A | 6/2005 |
| WO | 9935972 A1 | 7/1999 |
| WO | 0237935 A2 | 5/2002 |
| WO | 02067783 A2 | 9/2002 |
| WO | 03042968 A1 | 5/2003 |
| WO | 03065949 A2 | 8/2003 |
| WO | 03077101 A2 | 9/2003 |
| WO | 2004008988 A2 | 1/2004 |
| WO | 2004061744 A2 | 7/2004 |
| WO | 2004069041 A2 | 8/2004 |
| WO | 2004070580 A2 | 8/2004 |
| WO | 2005023120 A1 | 3/2005 |
| WO | 2005089681 A2 | 9/2005 |
| WO | 2005119505 A2 | 12/2005 |

OTHER PUBLICATIONS

Medical Advisory Secretariat, Computer-Assisted Hip and Knee Arthroplasty. Navigation and Active Robotic Systems, Feb. 2004, Ontario Health Technology Assessment Series 2004, vol. 4, No. 2, pp. 1-39, https://www.hqontario.ca/Portals/0/Documents/evidence/reports/rev_arthro_020104.pdf (Year: 2004).*

European Search Report for European Patent Application No. 06251808.9-2310, dated Jul. 14, 2006, 3 pages.

European Search Report for European Patent Application No. 06253685.9-2318, dated Dec. 12, 2006, 4 pages.

European Search Report for European Patent Application No. 06255072.8-2318, dated Jan. 25, 2007, 9 pages.

Japanese Office Action, Patent Application No. 2006194558, dated Nov. 1, 2011, pp. 1-3.

English translation of patent abstract for Japanese publication No. 2002291706, 1 page.

"The Vision and Reality of Wearable Computing", XP002399700, Apr. 1, 2004, 4 pages.

Carter et al., "Determination of Accuracy of Preoperative Templating of Noncemented Femoral Prosthesis," The Journal of Arthoplastry, vol. 10, No. 4, 1995, pp. 507-513.

* cited by examiner

SYSTEM AND METHOD FOR PERFORMING A COMPUTER ASSISTED ORTHOPAEDIC SURGICAL PROCEDURE

This application is a continuation application of U.S. patent application Ser. No. 15/082,000, which is a continuation application of U.S. patent application Ser. No. 14/104,216, now U.S. Pat. No. 9,299,117, which is a continuation application of U.S. patent application Ser. No. 11/420,244, now U.S. Pat. No. 8,635,082, entitled "Method and System for Managing Inventories of Orthopaedic Implants," which was filed on May 25, 2006. U.S. patent application Ser. Nos. 14/104,216 and 11/420,244 incorporated by reference the entirety of U.S. Utility patent application Ser. No. 11/241,530 entitled "System and Method for Performing a Computer Assisted Orthopaedic Surgical Procedure," which was filed Sep. 30, 2005 by Mark R. DiSilvestro et al. The entirety of each of U.S. patent application Ser. Nos. 15/082,000; 14/104,216; 11/420,244; and 11/241,530 is expressly incorporated herein by reference.

CROSS-REFERENCE TO RELATED U.S. PATENT APPLICATION

Cross-reference is made to U.S. Utility patent application Ser. No. 11/182,350 entitled "System and Method for Providing Orthopaedic Surgical Information to a Surgeon," which was filed Jul. 15, 2005 by Mark A. Heldreth et al., the entirety of which is expressly incorporated herein by reference.

TECHNICAL FIELD

The present disclosure relates generally to computer assisted surgery systems for use in the performance of orthopaedic procedures.

BACKGROUND

There is an increasing adoption of minimally invasive orthopaedic procedures. Because such surgical procedures generally restrict the surgeon's ability to see the operative area, surgeons are increasingly relying on computer systems, such as computer assisted orthopaedic surgery (CAOS) systems, to assist in the surgical operation. CAOS systems assist surgeons in the performance of orthopaedic surgical procedures by, for example, displaying images illustrating surgical steps of the surgical procedure being performed. Typical CAOS systems are stand-alone systems that are neither integrated with, nor configured to communicate with, other electronic systems or networks such as, for example, hospital networks. As such, typical CAOS systems are unable to access electronic data, such as medical records and the like, stored in the other electronic systems and networks.

SUMMARY

According to one aspect, a method for operating a computer assisted orthopaedic surgery system may include retrieving pre-operative data related to an orthopaedic surgical procedure to be performed on a patient from an electronic file. The pre-operative data may be retrieved from, for example, a remote computer such as a computer located in the surgeon's office or hospital and/or from a removable memory device. The method may also include selecting a number of images from an electronic library of instructional images based on the pre-operative data. The instructional images may be, for example, rendered images of individual surgical steps, images of orthopaedic surgical tools that are to be used, images containing orthopaedic surgical procedure information, or the like. The method may also include ordering the selected number of images. The ordered, selected number of images may form a workflow plan. The method may further include displaying the number of images during the orthopaedic surgical procedure on a display device. The method may also include displaying indicia of a location of an orthopaedic surgical tool on the display device. The method may further include receiving patient-related data. The number of images may be selected and ordered based on the patient-related data. The method may include displaying the pre-operative data and/or the patient-related data to the surgeon in response to a request received from the surgeon. The method may also include recording screenshots of a selection of the number of images, recording selection data indicative of selections made by the surgeon via the controller during the orthopaedic surgical procedure, and recording verbal surgical notes received by the controller from the surgeon via a microphone. Such recorded data may be stored in the computer assisted orthopaedic surgery system or may be transmitted to a hospital network and stored, for example, in a database included therein.

According to another aspect of the invention, a computer assisted orthopaedic surgery system may include a display device, processor, and memory device. The memory device may have a plurality of instructions stored therein. The instructions, when executed by the processor, may cause the processor to retrieve pre-operative data related to an orthopaedic surgical procedure to be performed on a patient form an electronic file. The instructions may also cause the processor to select a number of images from an electronic library of instructional images based on the pre-operative data and display the number of images on the display device. The number of images may be ordered by the processor before the images are displayed. The instructions may further cause the processor to retrieve patient-related data from an electronic file. In some embodiments, the number of images are selected and ordered based on the patient-related data. The pre-operative data and/or patient related data may be retrieved from a remote computer such as a computer which forms a portion of a hospital network and/or from a computer located at an office of the surgeon performing the procedure. Additionally, the data may be retrieved from a removable memory device, disk, or other data device. The instructions may further cause the processor to display a portion of the pre-operative data and/or patient related data to the surgeon upon request via the display device. The instructions may also cause the processor to determine deviation from the orthopaedic surgical procedure performed by the surgeon and may store the deviations for later review, record verbal surgical notes provided to the system by the surgeon via a microphone, record the surgical procedure selections chosen by the surgeon during the performance of the orthopaedic surgical procedure, and/or record screenshots of the images displayed to the surgeon via the display device. Such screenshots may be recorded automatically or via a request received from the surgeon.

In some embodiments, the computer assisted orthopaedic surgery system may be configured to communicate with a hospital network. The computer assisted orthopaedic surgery system may store surgical data in a database of the hospital network. Such surgical data may include the pre-operative data, the patient-related data, the recorded deviations, the recorded screenshots, the recorded verbal surgical notes or plain-text versions thereof converted by, for example, a voice recognition device or software, the recorded surgeon's selections, and/or other data related to the orthopaedic surgical procedure.

The above and other features of the present disclosure, which alone or in any combination may comprise patentable subject matter, will become apparent from the following description and the attached drawings.

BRIEF DESCRIPTION OF THE DRAWINGS

The detailed description particularly refers to the following figures, in which.

DETAILED DESCRIPTION OF THE DRAWINGS

Figure 1:
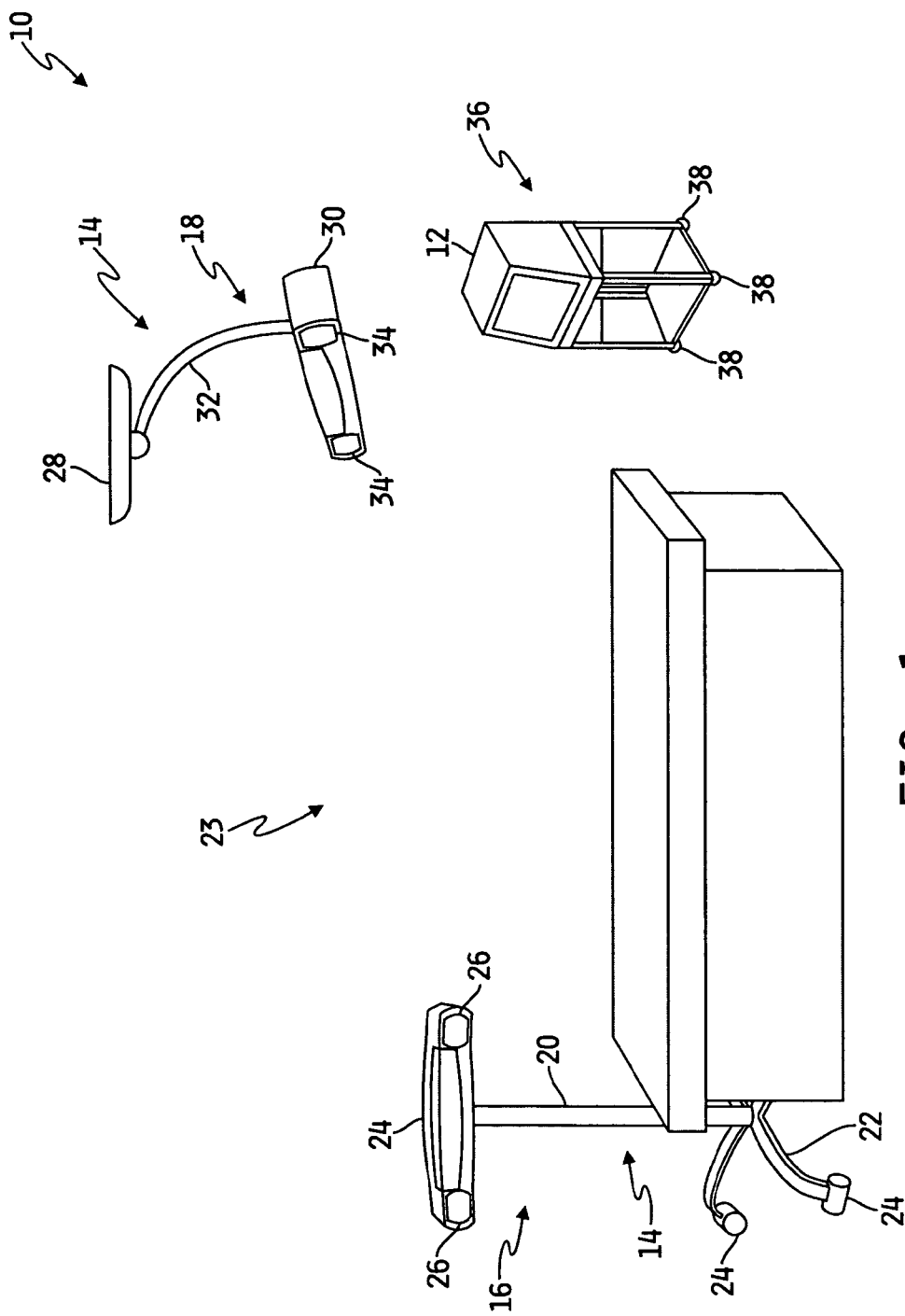
FIG. 1 is a perspective view of a computer assisted orthopaedic surgery (CAOS) system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a computer assisted orthopaedic surgery (CAOS) system 10 includes a computer 12 and a camera unit 14. The CAOS system 10 may be embodied as any type of computer assisted orthopaedic surgery system. Illustratively, the CAOS system 10 is embodied as a Ci™ system commercially available from DePuy Orthopaedics, Inc. of Warsaw, Ind. The camera unit 14 may be embodied as a mobile camera unit 16 or a fixed camera unit 18. In some embodiments, the system 10 may include both types of camera units 16, 18. The mobile camera unit 16 includes a stand 20 coupled with a base 22. The base 22 may include a number of wheels 24 to allow the mobile camera unit 16 to be repositioned within a hospital room 23. The mobile camera unit 16 includes a camera head 24. The camera head 24 includes two cameras 26. The camera head 24 may be positionable relative to the stand 20 such that the field of view of the cameras 26 may be adjusted. The fixed camera unit 18 is similar to the mobile camera unit 16 and includes a base 28, a camera head 30, and an arm 32 coupling the camera head 28 with the base 28. In some embodiments, other peripherals, such as display screens, lights, and the like, may also be coupled with the base 28. The camera head 30 includes two cameras 34. The fixed camera unit 18 may be coupled to a ceiling, as illustratively shown in FIG. 1, or a wall of the hospital room. Similar to the camera head 24 of the camera unit 16, the camera head 30 may be positionable relative to the arm 32 such that the field of view of the cameras 34 may be adjusted. The camera units 14, 16, 18 are communicatively coupled with the computer 12. The computer 12 may be mounted on or otherwise coupled with a cart 36 having a number of wheels 38 to allow the computer 12 to be positioned near the surgeon during the performance of the orthopaedic surgical procedure.

Figure 2:
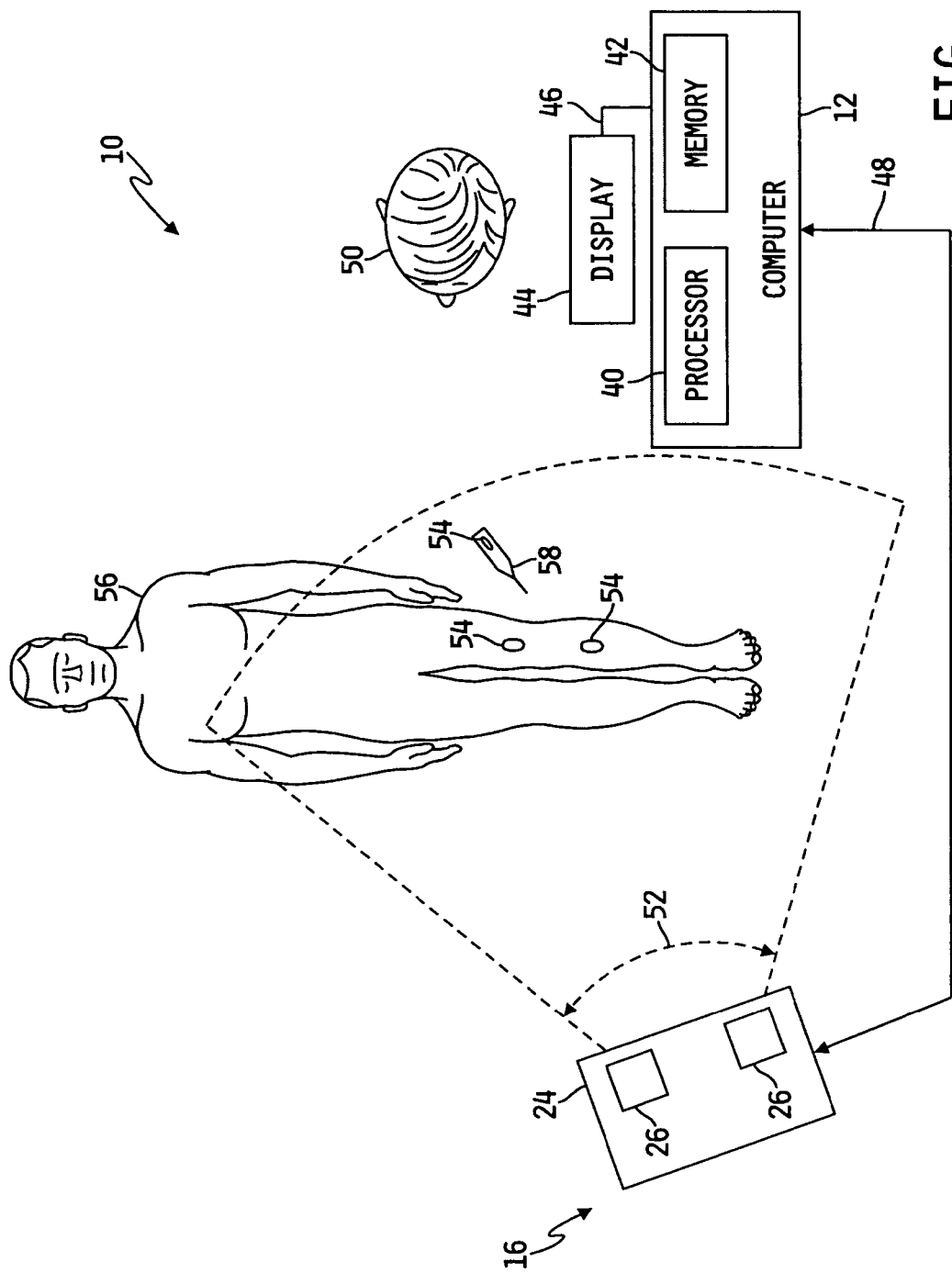
FIG. 2 is a simplified diagram of the CAOS system of FIG. 1.

Referring now to FIG. 2, the computer 12 illustratively includes a processor 40 and a memory device 42. The processor 40 may be embodied as any type of processor including, for example, discrete processing circuitry (e.g., a collection of logic devices), general purpose integrated circuit(s), and/or application specific integrated circuit(s) (i.e., ASICs). The memory device 42 may be embodied as any type of memory device and may include one or more memory types, such as, random access memory (i.e., RAM) and/or read-only memory (i.e., ROM). In addition, the computer 12 may include other devices and circuitry typically found in a computer for performing the functions described herein such as, for example, a hard drive, input/output circuitry, and the like.

The computer 12 is communicatively coupled with a display device 44 via a communication link 46. Although illustrated in FIG. 2 as separate from the computer 12, the display device 44 may form a portion of the computer 12 in some embodiments. Additionally, in some embodiments, the display device 44 or an additional display device may be positioned away from the computer 12. For example, the display device 44 may be coupled with the ceiling or wall of the operating room wherein the orthopaedic surgical procedure is to be performed. Additionally or alternatively, the display device 44 may be embodied as a virtual display such as a holographic display, a body mounted display such as a heads-up display, or the like. The computer 12 may also be coupled with a number of input devices such as a keyboard and/or a mouse for providing data input to the computer 12. However, in the illustrative embodiment, the display device 44 is a touch-screen display device capable of receiving inputs from an orthopaedic surgeon 50. That is, the surgeon 50 can provide input data to the computer 12, such as making a selection from a number of on-screen choices, by simply touching the screen of the display device 44.

The computer 12 is also communicatively coupled with the camera unit 16 (and/or 18) via a communication link 48. Illustratively, the communication link 48 is a wired communication link but, in some embodiments, may be embodied as a wireless communication link. In embodiments wherein the communication link 48 is a wireless signal path, the camera unit 16 and the computer 12 include wireless transceivers such that the computer 12 and camera unit 16 can transmit and receive data (e.g., image data). Although only the mobile camera unit 16 is shown in FIG. 2, it should be appreciated that the fixed camera unit 18 may alternatively be used or may be used in addition to the mobile camera unit 16.

Figure 3:
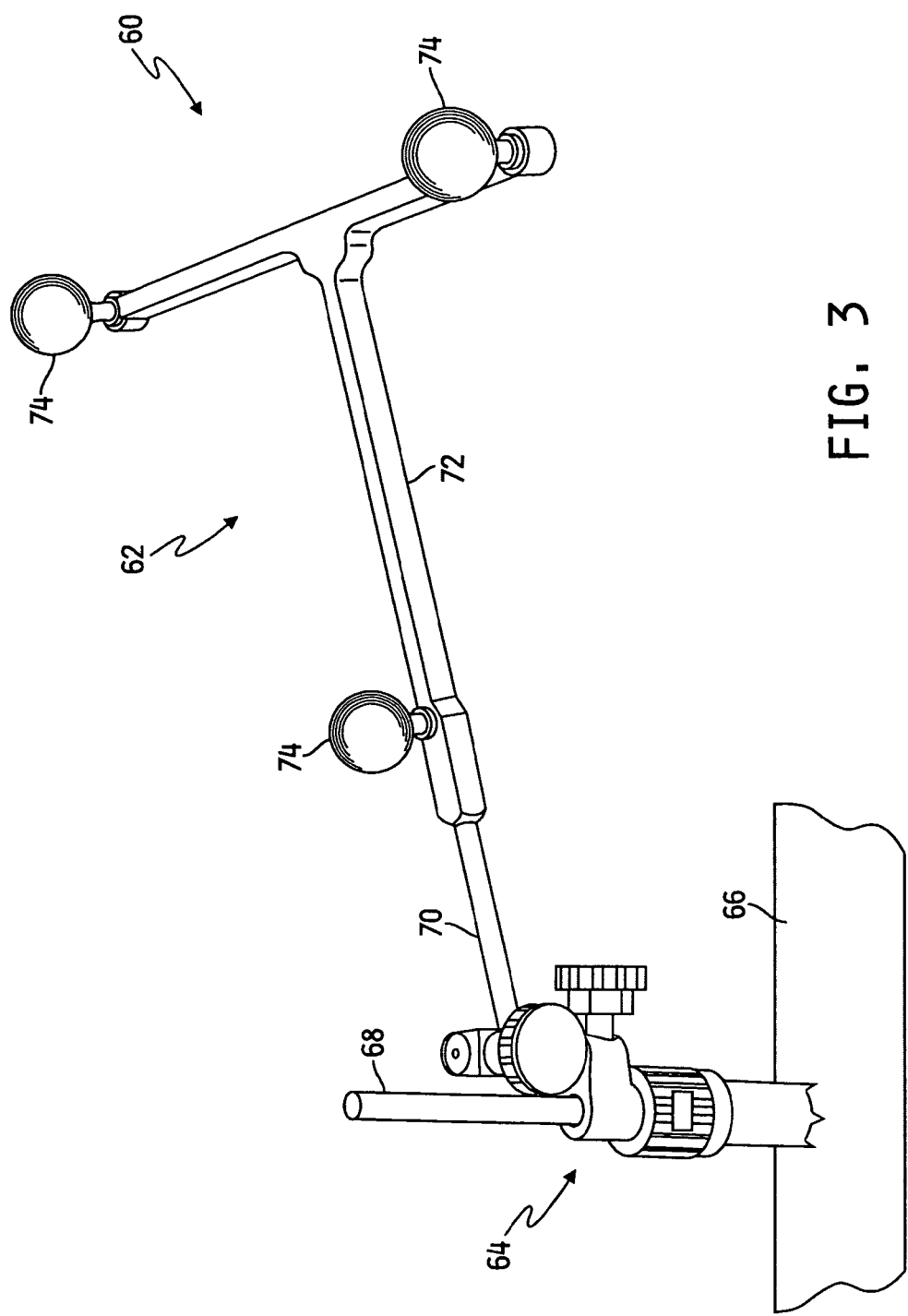
FIG. 3 is a perspective view of a bone locator tool.

The CAOS system 10 may also include a number of sensors or sensor arrays 54 which may be coupled the relevant bones of a patient 56 and/or with orthopaedic surgical tools 58. For example, as illustrated in FIG. 3, a tibial array 60 includes a sensor array 62 and bone clamp 64. The illustrative bone clamp 64 is configured to be coupled with a tibia bone 66 of the patient 56 using a Schantz pin 68, but other types of bone clamps may be used. The sensor array 62 is coupled with the bone clamp 64 via an extension arm 70. The sensor array 62 includes a frame 72 and three reflective elements or sensors 74. The reflective elements 74 are embodied as spheres in the illustrative embodiment, but may have other geometric shapes in other embodiments. Additionally, in other embodiments sensor arrays having more than three reflective elements may be used. The reflective elements 74 are positioned in a predefined configuration that that allows the computer 12 to determine the identity of the tibial array 60 based on the configuration. That is, when the tibial array 60 is positioned in a field of view 52 of the camera head 24, as shown in FIG. 2, the computer 12 is configured to determine the identity of the tibial array 60 based on the images received from the camera head 24. Additionally, based on the relative position of the reflective elements 74, the computer 12 is configured to determine the location and orientation of the tibial array 60 and, accordingly, the tibia 66 to which the array 60 is coupled.

Figure 4:
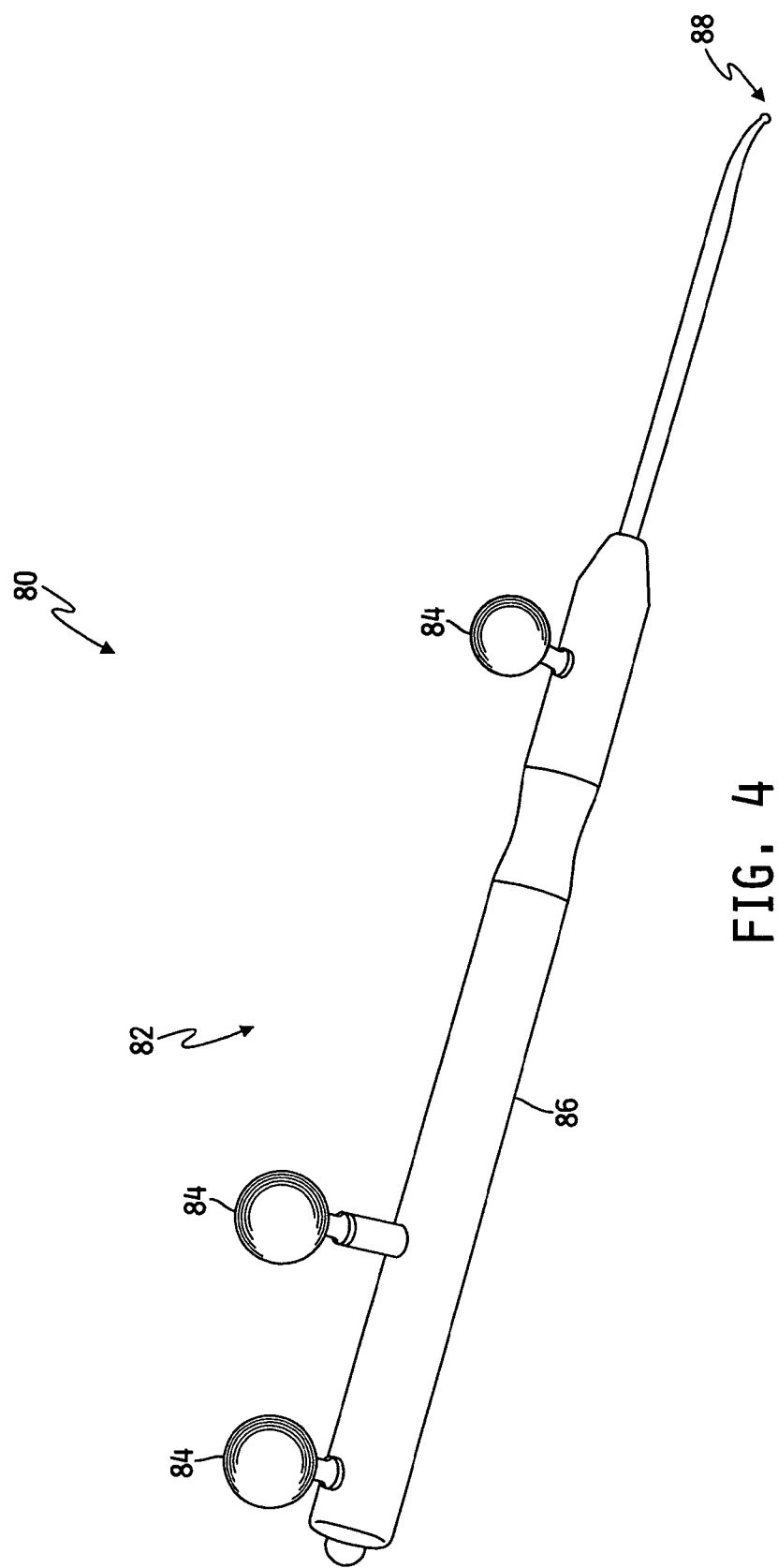
FIG. 4 is a perspective view of a registration tool for use with the system of FIG. 1.
Figure 5:
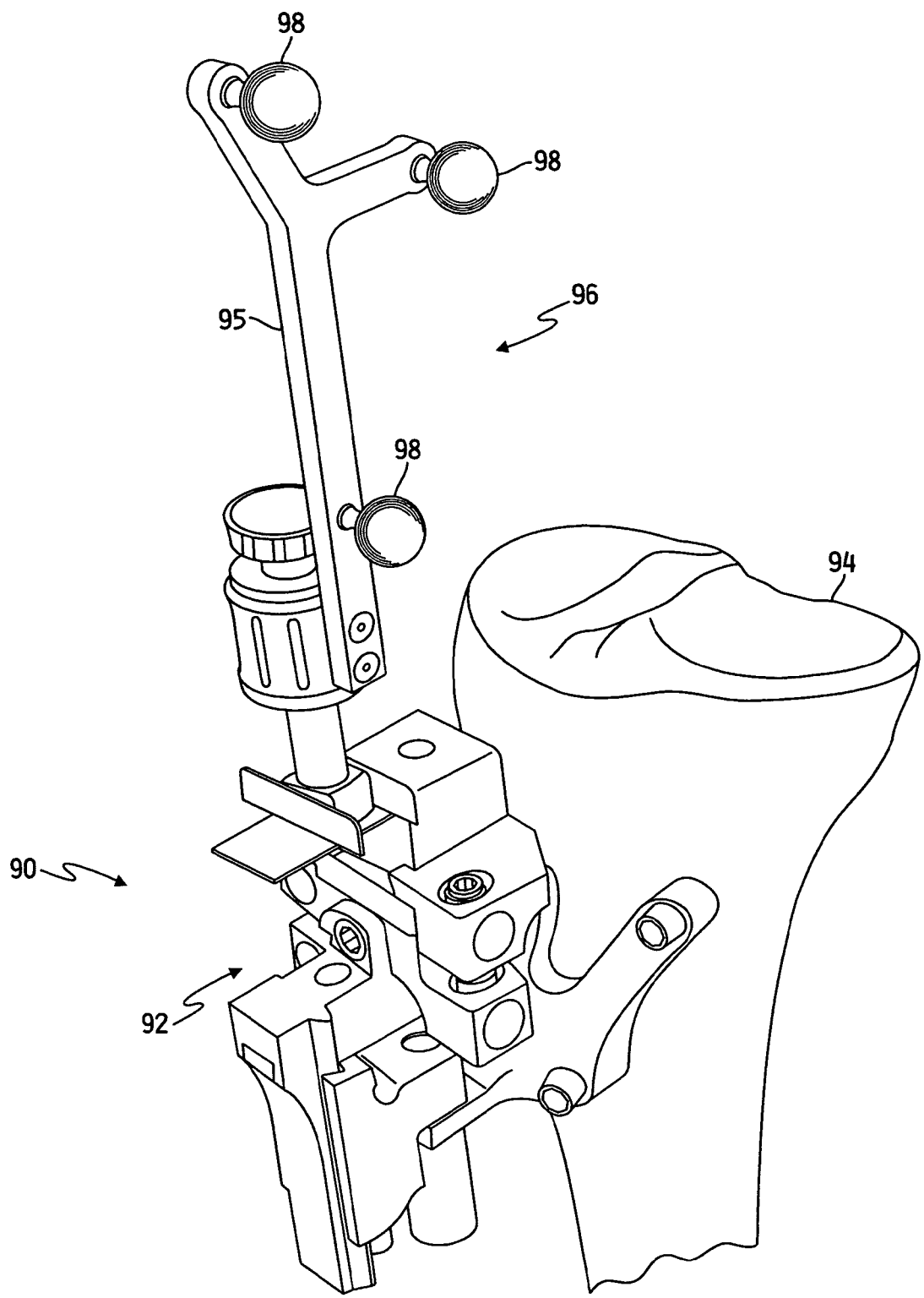
FIG. 5 is a perspective view of an orthopaedic surgical tool for use with the system of FIG. 1.
Figure 7:
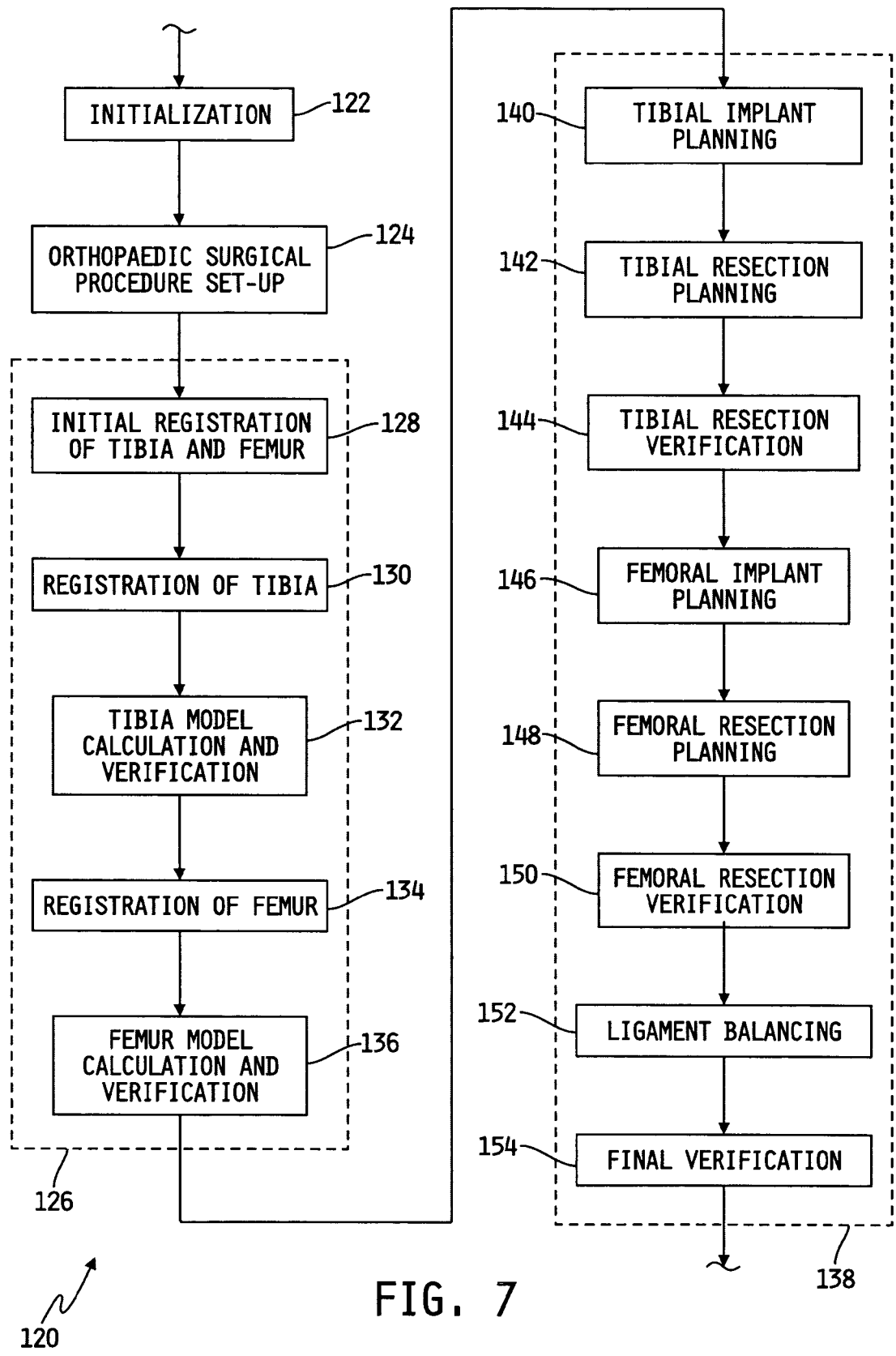
FIG. 7 is a simplified flowchart diagram of one particular embodiment of the algorithm of FIG. 6.

Sensor arrays may also be coupled to other surgical tools. For example, a registration tool 80, as shown in FIG. 4, is used to register points of a bone as discussed in more detail below in regard to FIG. 7. The registration tool 80 includes a sensor array 82 having three reflective elements 84 coupled with a handle 86 of the tool 80. The registration tool 80 also includes pointer end 88 that is used to register points of a bone. The reflective elements 84 are also positioned in a configuration that allows the computer 12 to determine the identity of the registration tool 80 and its relative location (i.e., the location of the pointer end 88). Additionally, sensor arrays may be used on other surgical tools such as a tibial resection jig 90, as illustrated in FIG. 5. The jig 90 includes a resection guide portion 92 that is coupled with a tibia bone 94 at a location of the bone 94 that is to be resected. The jig 90 includes a sensor array 96 that is coupled with the portion 92 via a frame 95. The sensor array 96 includes three reflective elements 98 that are positioned in a configuration that allows the computer 12 to determine the identity of the jig 90 and its relative location (e.g., with respect to the tibia bone 94).

The CAOS system 10 may be used by the orthopaedic surgeon 50 to assist in any type of orthopaedic surgical procedure including, for example, a total knee replacement procedure. To do so, the computer 12 and/or the display device 44 are positioned within the view of the surgeon 50. As discussed above, the computer 12 may be coupled with a movable cart 36 to facilitate such positioning. The camera unit 16 (and/or camera unit 18) is positioned such that the field of view 52 of the camera head 24 covers the portion of a patient 54 upon which the orthopaedic surgical procedure is to be performed, as shown in FIG. 2.

During the performance of the orthopaedic surgical procedure, the computer 12 of the CAOS system 10 is programmed or otherwise configured to display images of the individual surgical procedure steps which form the orthopaedic surgical procedure being performed. The images may be graphically rendered images or graphically enhanced photographic images. For example, the images may include three dimensional rendered images of the relevant anatomical portions of a patient. The surgeon 50 may interact with the computer 12 to display the images of the various surgical steps in sequential order. In addition, the surgeon may interact with the computer 12 to view previously displayed images of surgical steps, selectively view images, instruct the computer 12 to render the anatomical result of a proposed surgical step or procedure, or perform other surgical related functions. For example, the surgeon may view rendered images of the resulting bone structure of different bone resection procedures. In this way, the CAOS system 10 provides a surgical "walk-through" for the surgeon 50 to follow while performing the orthopaedic surgical procedure.

In some embodiments, the surgeon 50 may also interact with the computer 12 to control various devices of the system 10. For example, the surgeon 50 may interact with the system 10 to control user preferences or settings of the display device 44. Further, the computer 12 may prompt the surgeon 50 for responses. For example, the computer 12 may prompt the surgeon to inquire if the surgeon has completed the current surgical step, if the surgeon would like to view other images, and the like.

The camera unit 16 and the computer 12 also cooperate to provide the surgeon with navigational data during the orthopaedic surgical procedure. That is, the computer 12 determines and displays the location of the relevant bones and the surgical tools 58 based on the data (e.g., images) received from the camera head 24 via the communication link 48. To do so, the computer 12 compares the image data received from each of the cameras 26 and determines the location and orientation of the bones and tools 58 based on the relative location and orientation of the sensor arrays 54, 62, 82, 96. The navigational data displayed to the surgeon 50 is continually updated. In this way, the CAOS system 10 provides visual feedback of the locations of relevant bones and surgical tools for the surgeon 50 to monitor while performing the orthopaedic surgical procedure.

Figure 6:
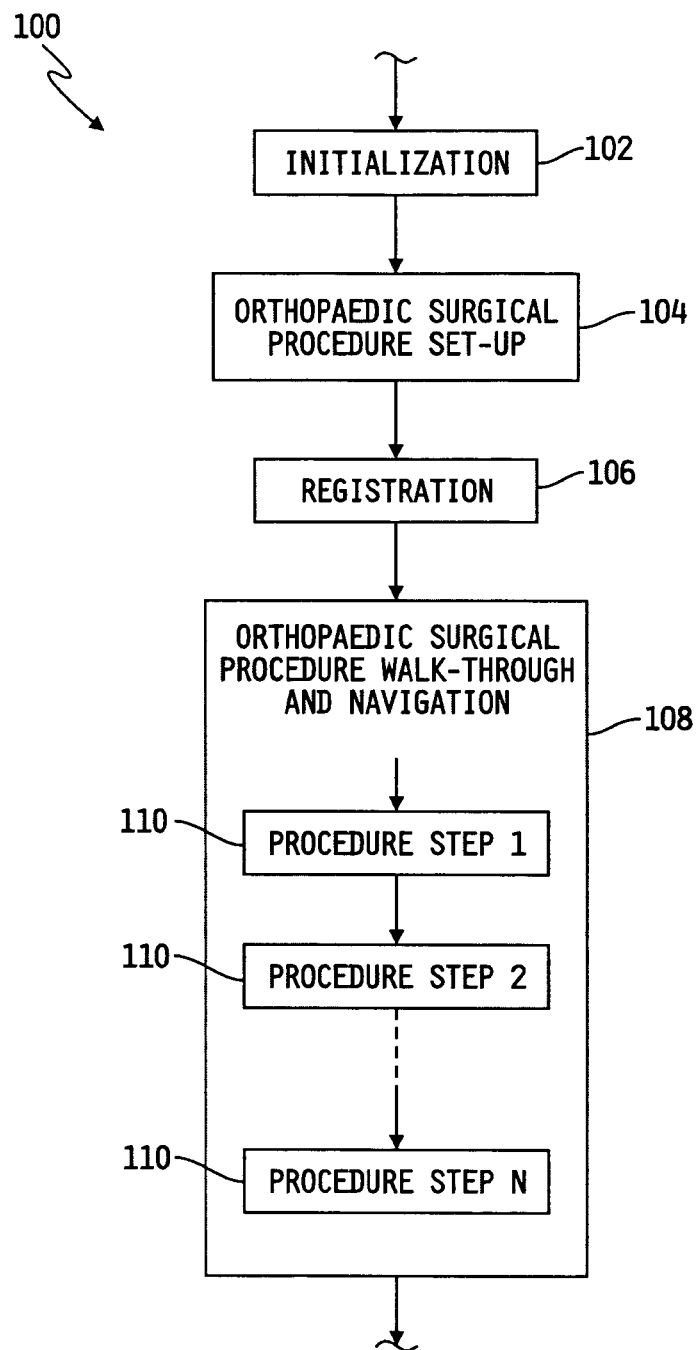
FIG. 6 is a simplified flowchart diagram of an algorithm that is used by the CAOS system of FIG. 1.

Referring now to FIG. 6, an algorithm 100 for assisting a surgeon in performing an orthopaedic surgical procedure is executed by the computer 12. The algorithm 100 begins with a process step 102 in which the CAOS system 10 is initialized. During process step 102, settings, preferences, and calibrations of the CAOS system 10 are established and performed. For example, the video settings of the display device 44 may be selected, the language displayed by the computer 12 may be chosen, and the touch screen of the display device 44 may be calibrated in process step 102.

In process step 104, the selections and preferences of the orthopaedic surgical procedure are chosen by the surgeon. Such selections may include the type of orthopaedic surgical procedure that is to be performed (e.g., a total knee arthroplasty), the type of orthopaedic implant that will be used (e.g., make, model, size, fixation type, etc.), the sequence of operation (e.g., the tibia or the femur first), and the like. Once the orthopaedic surgical procedure has been set up in process step 104, the bones of the patient are registered in process step 106. To do so, sensor arrays, such as the tibial array 60 illustrated in FIG. 3, are coupled with the relevant bones of the patient (i.e., the bones involved in the orthopaedic surgical procedure). Additionally, the contours of such bones are registered using the registration tool 80. To do so, the pointer end 88 of the tool 80 is touched to various areas of the bones to be registered. In response to the registration, the computer 12 displays rendered images of the bones wherein the location and orientation of the bones are determined based on the sensor arrays coupled therewith and the contours of the bones are determined based on the registered points. Because only a selection of the points of the bone is registered, the computer 12 calculates and renders the remaining areas of the bones that are not registered with the tool 80.

Figure 8:
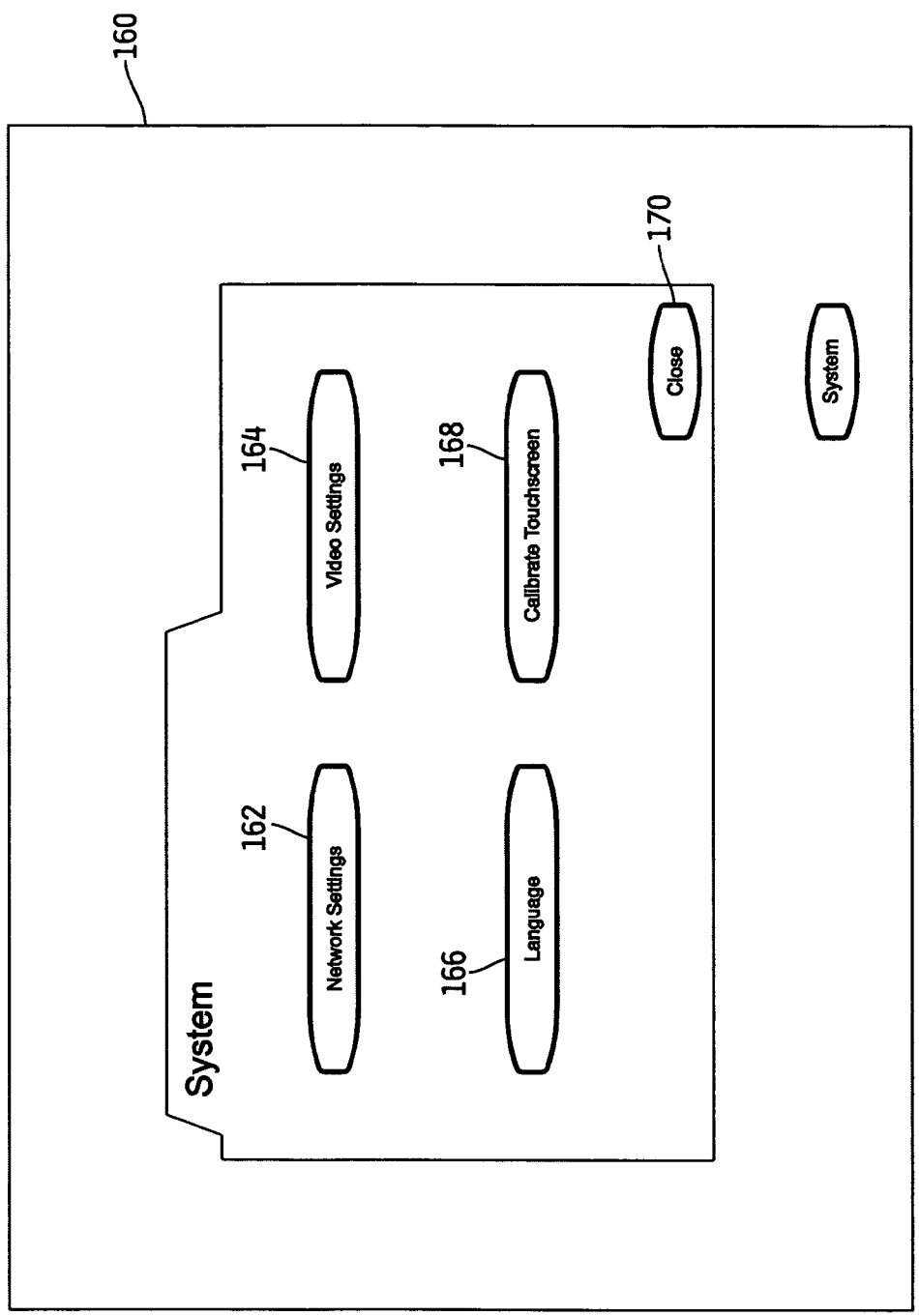
FIGS. 8-17 illustrate various screen images that are displayed to a surgeon during the operation of the system of FIG. 1

Once the pertinent bones have been registered in process step 106, the computer 12, in cooperation with the camera unit 16, 18, displays the images of the surgical steps of the orthopaedic surgical procedure and associated navigation data (e.g., location of surgical tools) in process step 108. To do so, the process step 108 includes a number of sub-steps 110 in which each surgical procedure step is displayed to the surgeon 50 in sequential order along with the associated navigational data. The particular sub-steps 110 that are displayed to the surgeon 50 may depend on the selections made by the surgeon 50 in the process step 104. For example, if the surgeon 50 opted to perform a particular procedure tibia-first, the sub-steps 110 are presented to the surgeon 50 in a tibia-first order Referring now to FIG. 7, in one particular embodiment, an algorithm 120 for assisting a surgeon in performing a total knee arthroplasty procedure may be executed by the computer 12. The algorithm 120 includes a process step 122 in which the CAOS system 10 is initialized. The process step 122 is similar to the process step 102 of the algorithm 100 described above in regard to FIG. 6. In process step 122, the preferences of the CAOS system 10 are selected and calibrations are set. To do so, the computer 12 displays a user initialization interface 160 to the surgeon 50 via the display device 44 as illustrated in FIG. 8. The surgeon 50 may interact with the interface 160 to select various initialization options of the CAOS system 10. For example, the surgeon 50 may select a network settings button 162 to change the network settings of the system 10, a video settings button 164 to change the video settings of the system 10, a language button 166 to change the language used by the system 10, and/or a calibration button 168 to change the calibrations of the touch screen of the display device 44. The surgeon 50 may select a button by, for example, touching an appropriate area of the touch screen of the display device 44, operating an input device such as a mouse to select the desired on-screen button, or the like.

Additional images and/or screen displays may be displayed to the surgeon 50 during the initialization process. For example, if the surgeon 50 selects the button 162, a network setting interface may be displayed on the device 44 to allow the surgeon 50 to select different values, connections, or other options to change the network settings. Once the CAOS system 10 has been initialized, the surgeon 50 may close the user initialization interface 160 by selecting a close button 170 and the algorithm 122 advances to the process step 124.

Figure 9:
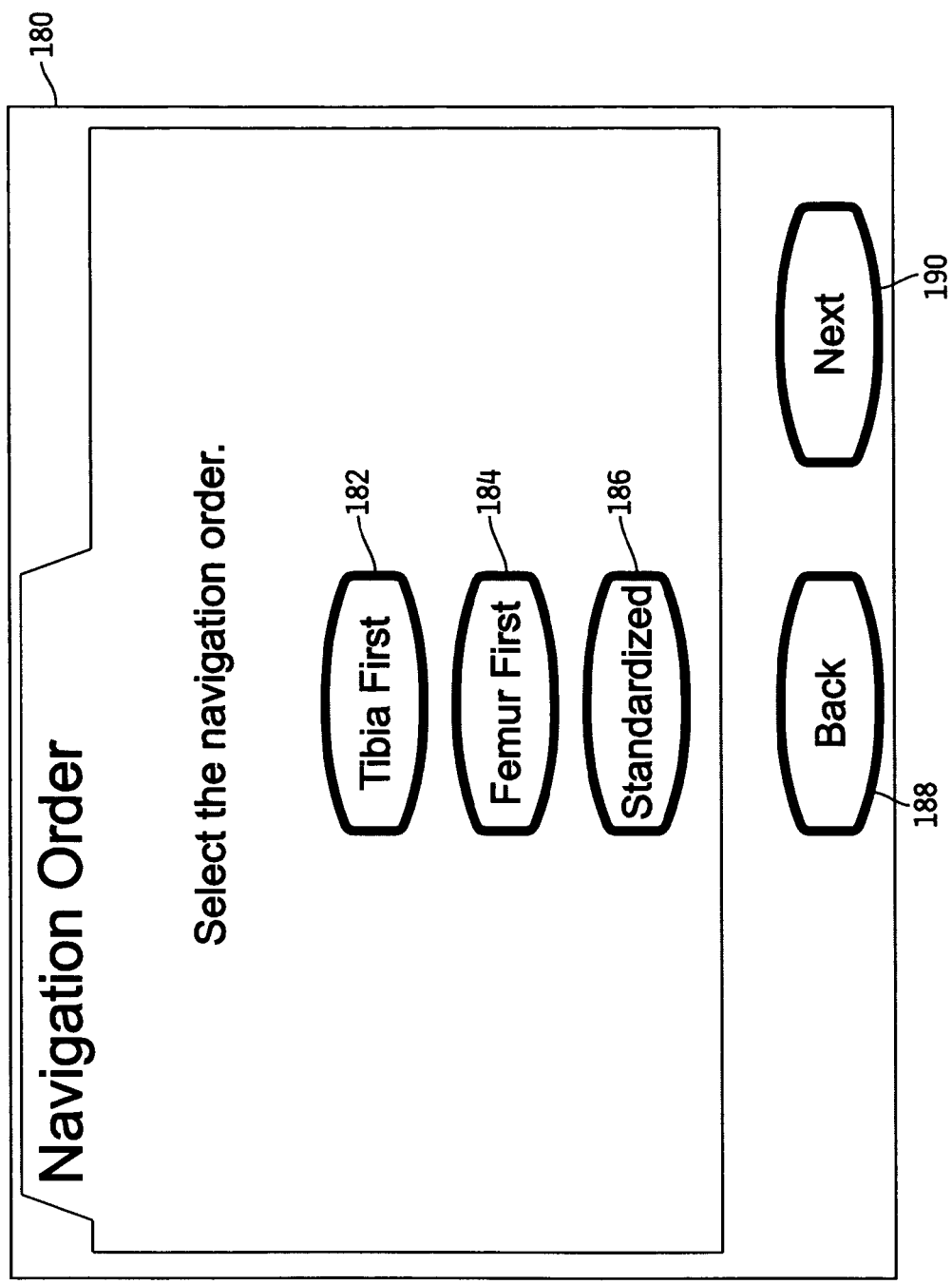

In process step 124, selections of the orthopaedic surgical procedure are chosen by the surgeon 50. The process step 124 is similar to the process step 104 of the algorithm 100 described above in regard to FIG. 6. For example, the selections made in the process step 104 may include, but are not limited to, the type of orthopaedic surgical procedure that is to be performed, the type of orthopaedic implant that will be used, and the sequence of operation, and the like. To do so, a number of procedure preference selection screens may be displayed to the surgeon 50 via the display device 44. For example, as illustrated in FIG. 9, a navigation order selection screen 180 may be displayed to the surgeon 50. The surgeon 50 may interact with the screen 180 to select the navigational (i.e., surgical) order of the orthopaedic surgical procedure being performed (i.e., a total knee arthroplasty procedure in the illustrative embodiment). For example, the surgeon 50 may select a button 182 to instruct the controller 12 that the tibia bone of the patient 56 will be operated on first, a button 184 to instruct the controller 12 that the femur bone will be operated on first, or a button 186 to select a standardized navigation order based on, for example, the type of orthopaedic implant being used. The surgeon 50 may also navigate among the selection screens by a back button 188 to review previously displayed orthopaedic surgical procedure set-up screens or a next button 190 to proceed to the next orthopaedic surgical procedure set-up screen. Once the surgeon 50 has selected the appropriate navigation order and/or other preferences and settings of the orthopaedic surgical procedure being performed, the algorithm 120 advances to the process step 126.

In the process step 126, the relevant bones of the patient 56 are registered. The process step 126 is similar to the registration process step 106 of the algorithm 100. The process step 126 includes a number of sub-steps 128-136 in which the bones of the patient 56 involved in the orthopaedic surgical procedure are registered. In process step 128, the relevant bones are initially registered. That is, in the illustrative algorithm 120, a tibia and a femur bone of the patient 56 are initially registered. To do so, a tibia array, such as the tibia array 60 illustrated in and described above in regard to FIG. 3, and a femur array are coupled with the respective bones. The tibia and femur arrays are coupled in the manner described above in regard to the tibia array 60. The camera head 24 of the camera unit 16 is adjusted such that the tibia and femur arrays are within the field of view 52 of the camera head 24. Once the arrays are coupled and the camera head 24 properly positioned, the tibia and femur of the patient 56 are initially registered.

Figure 10:
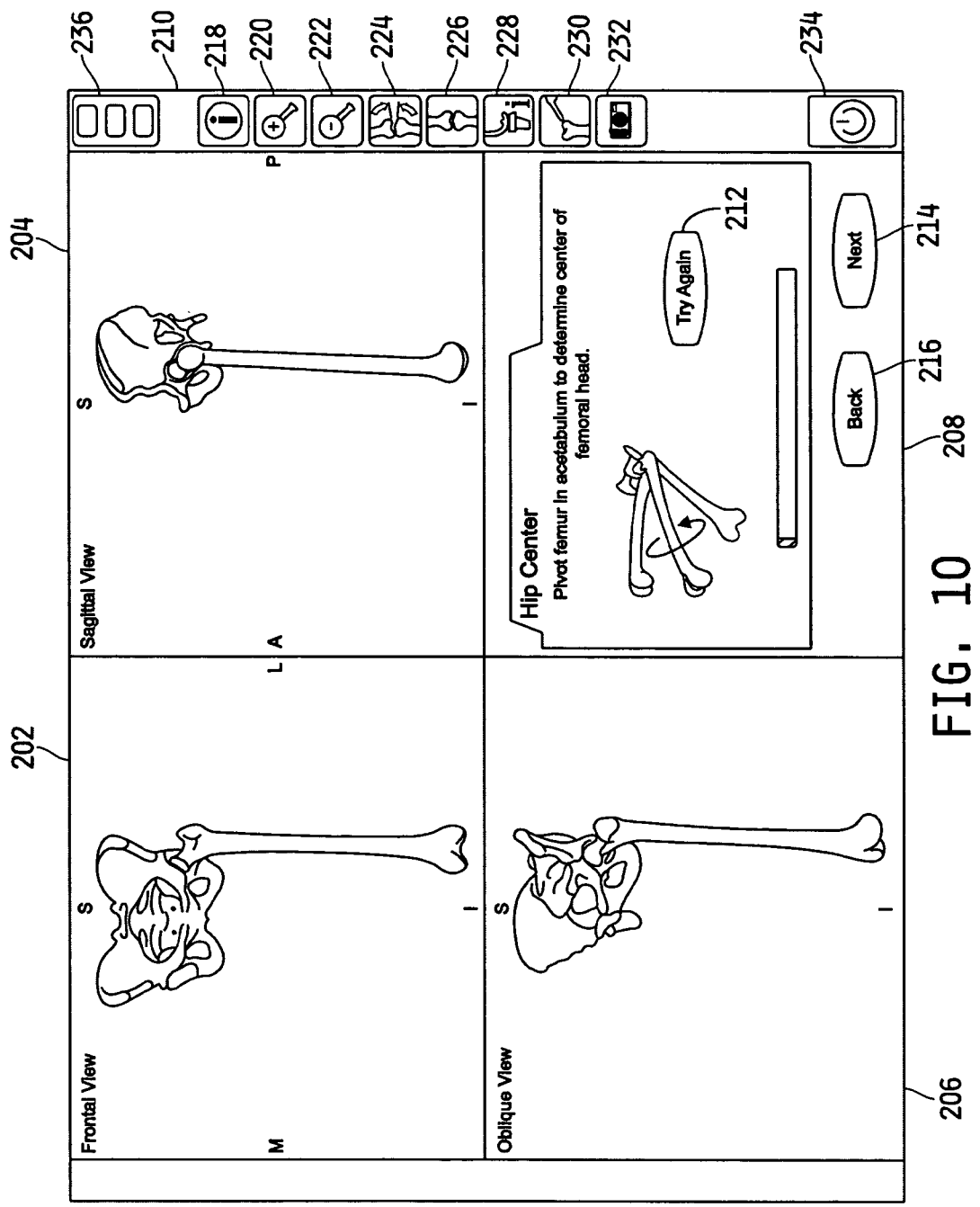

To do so, the controller 12 displays a user interface 200 to the surgeon 50 via the display device 44, as shown in FIG. 10. The interface 200 includes several navigation panes 202, 204, 206, a surgical step pane 208, and a tool bar 210. Navigational data is displayed to the surgeon 50 in the navigation panes 202, 204, 206. The computer 12 displays different views of the bone and/or surgical tools 58 in each of the panes 202, 204, 206. For example, a frontal view of the patient's 56 hip and femur bone is displayed in the navigation pane 202, a sagittal view of the patient's 56 bones is displayed in the navigation pane 204, and an oblique view of the patient's 56 bones is displayed in the navigation pane 206.

The computer 12 displays the surgical procedure steps in the pane 208. For example, in FIG. 10, the computer 12 is requesting the leg of the patient 56 be moved about in a circular motion such that the femur bone of the patient 56 is initially registered. In response, the computer 12 determines the base location and orientation of the femur bone (e.g., the femur head) of the patient 56 based on the motion of the sensor array 54 coupled with the bone (i.e., based on the image data of the sensor array 54 received from the camera head 24). Although only the femur bone is illustrated in FIG. 10 as being initially registered, it should be appreciated that the tibia bone is also initially registered and that other images and display screen are displayed to the surgeon 50 during such initial registration.

The surgeon 50 can attempt to initially register the bones as many times as required by selecting a "try again" button 212. Once the relevant bones have been initially registered, the surgeon 50 can advance to the next surgical procedure step of the registration step 126 by selecting the next button 214. Alternatively, the surgeon 50 can skip one or more of the initial registration steps by selecting the button 214 and advancing to the next surgical procedure step while not performing the initial registration step (e.g., by not initially registering the femur bone of the patient 56). The surgeon 50 may also go back to the previous surgical procedure step (e.g., the initial registration of the tibia) by selecting a back button 216. In this way, the surgeon 50 can navigate through the surgical setup, registration, and procedure steps via the buttons 214, 216.

The toolbar 210 includes a number of individual buttons, which may be selected by the surgeon 50 during the performance of the orthopaedic surgical procedure. For example, the toolbar 210 includes an information button 218 that may be selected to retrieve and display information on the application software program being executed by the computer 12 such as the version number, "hotline" phone numbers, and website links. The toolbar 210 also includes zoom buttons 220 and 222. The zoom button 220 may be selected by the surgeon 50 to zoom in on the rendered images displayed in the panes 202, 204, 206 and the zoom button 222 may be used to zoom out. A ligament balancing button 224 may be selected to proceed to a ligament balancing procedure, which is described in more detail below in regard to process step 152. A 3D model button 226 may be selected to alternate between the displaying of the rendered bone (e.g., femur or tibia) and displaying only the registered points of the rendered bone in the navigation panes 202, 204, and 206. An implant information button 228 may be selected to display information related to an orthopaedic implant selected during later steps of the orthopaedic surgical procedure (e.g., process steps 140 and 146 described below). Such information may include, for example, the make, type, and size of the orthopaedic implant. A registration verification button 230 may be selected by the surgeon 50 at any time during the procedure to verify the rendered graphical model of a bone if, for example, the sensor arrays 54 coupled with the bone are accidentally bumped or otherwise moved from their fixed position. A screenshot button 232 may also be selected by the surgeon 50 at any time during the performance of the orthopaedic surgical procedure to record and store a screenshot of the images displayed to the surgeon 50 at that time. The screenshots 50 may be recorded in a storage device, such as a hard drive, of the computer 12. A close button 234 may be selected to end the current navigation and surgical procedure walk-through. After selecting the button 234, any information related to the orthopaedic surgical procedure that has been recorded, such as screenshots and other data, are stored in the storage device of the computer 12 for later retrieval and review.

The toolbar 210 also includes a status display 236. The status display 236 displays different color lights that indicate whether the system 10 can "see" or otherwise detect the sensor arrays 54 coupled with the bones and/or surgical tools. The status display 236 is also a button that may be selected to view a help screen illustrating a graphical rendering of the field of view 52 of the camera head 24 such that the positioning of the camera unit 16 and the sensor arrays 54 and surgical tools 58 can be monitored and adjusted if needed.

Figure 11:
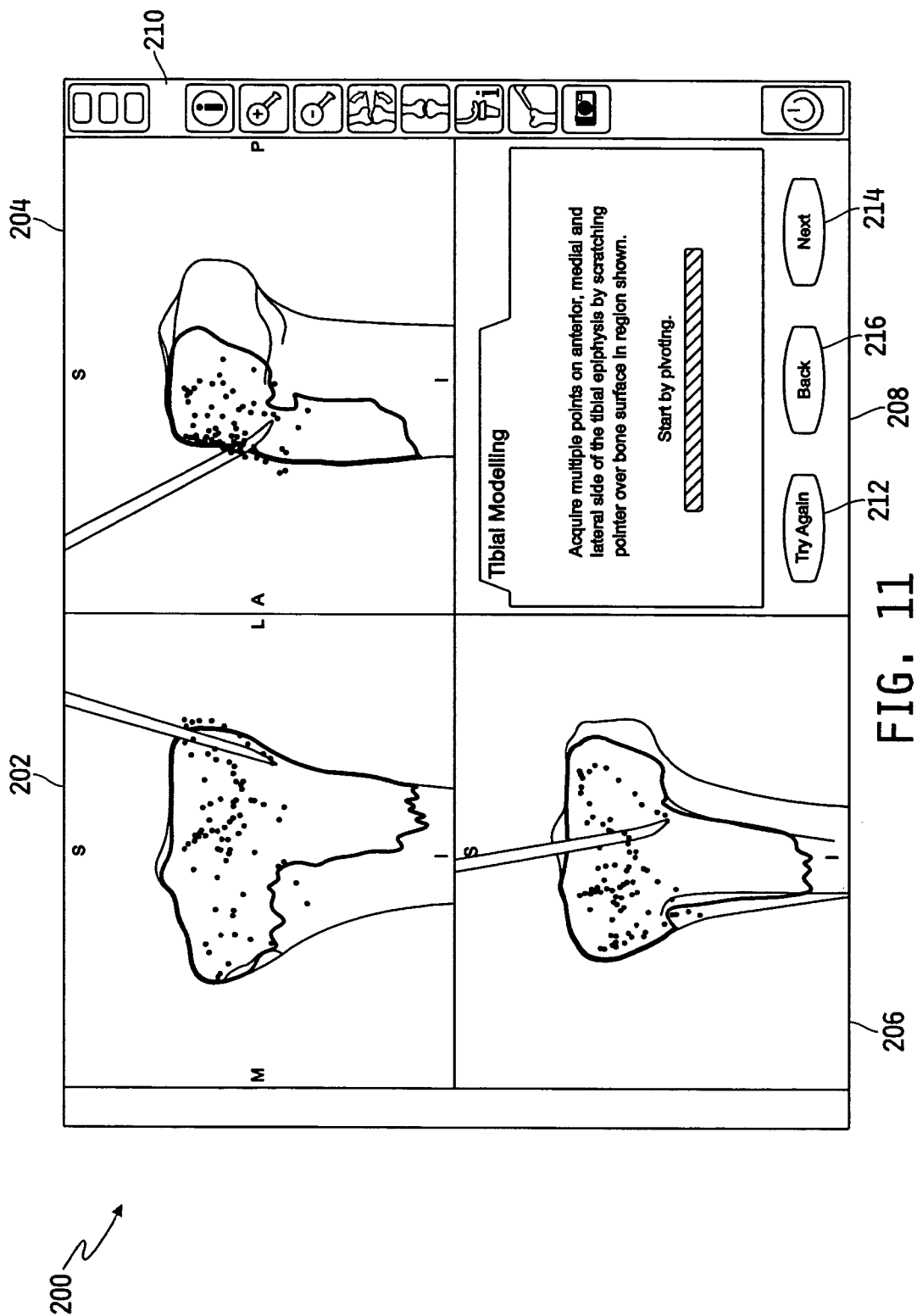

Once the initial registration of the tibia and femur bones of the patient 56 is complete, the algorithm 120 advances to process step 130 in which the contour of the proximal tibia of the patient 56 is registered. To do so, the surgeon 50 uses a registration tool, such as the registration tool 80 illustrated in and described above in regard to FIG. 4. As illustrated in FIG. 11, the surgeon 50 registers the proximal tibia by placing the pointer end 88 of the registration tool 80 on the surface of the tibia bone as instructed in the surgical step pane 208. Contour points of the tibia bone are recorded by the computer 12 periodically as the pointer end 88 is dragged across the surface of the tibia bone and/or placed in contact with the tibia bone. The surgeon 50 registers enough points on the proximal tibia such that the computer 12 can determine and display a relatively accurate rendered model of the relevant portions of the tibia bone. Portions of the tibia bone that are not registered, but rather rendered by the computer 12 based on a predetermined model of the tibia bone, are displayed to the surgeon 50 in a different color than the registered portions of the tibia bone. In this way, the surgeon 50 can monitor the registration of the tibia bone and ensure that all relevant portions of the tibia bone have been registered to improve the accuracy of the displayed model.

Figure 12:
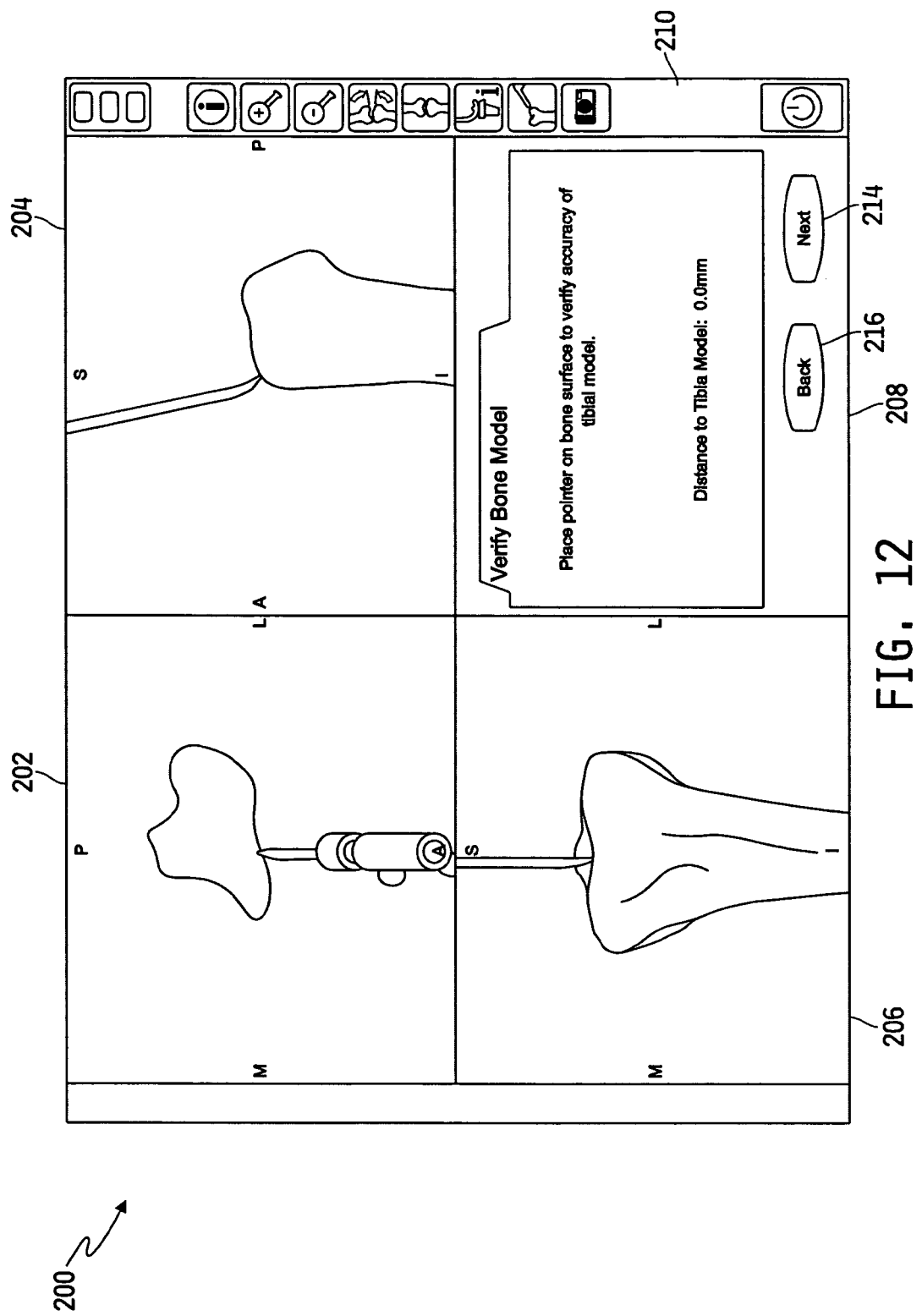

Once all the relevant portions of the proximal tibia have been registered in process step 130, the tibia model is calculated and verified in process step 132. To do so, the surgeon 50 follows the instructions provided in the surgical step pane 208. The proximal tibia is verified by touching the pointer end 88 of the registration tool 80 to the registered portions of the tibia bone and monitoring the distance data displayed in the pane 208 as illustrated in FIG. 12. Based on the distance data, the surgeon 50 can determine if the current tibia model is accurate enough for the orthopaedic surgical procedure. If not, the surgeon 50 can redo the registration of the proximal tibia or supplement the registration data with additional registration points by selecting the back button 216. Once the model of the patient's 56 tibia has been determined to be sufficiently accurate, the surgeon 50 may proceed by selecting the next button 214.

The distal femur of the patient 56 is registered next in the process step 134. The registration of the femur in process step 134 is similar to the registration of the tibia in the process step 130. That is, the registration tool 80 is used to registered data points on the distal femur. Once the registration of the femur is complete, the femur model is calculated and verified in process step 136. The verification of the femur in process step 136 is similar to the verification of the tibia in process step 132. The registration tool 80 may be used to touch pre-determined portions of the femur to determine the accuracy of the femur model. Based on the distance data displayed in the surgical step pane 208, the surgeon 50 may reregister the femur or add addition registration data points to the model by selecting the back button 216. Once the femur bone model is verified, the surgeon 50 can proceed with the orthopaedic surgical procedure by selecting the next button 214.

Figure 13:
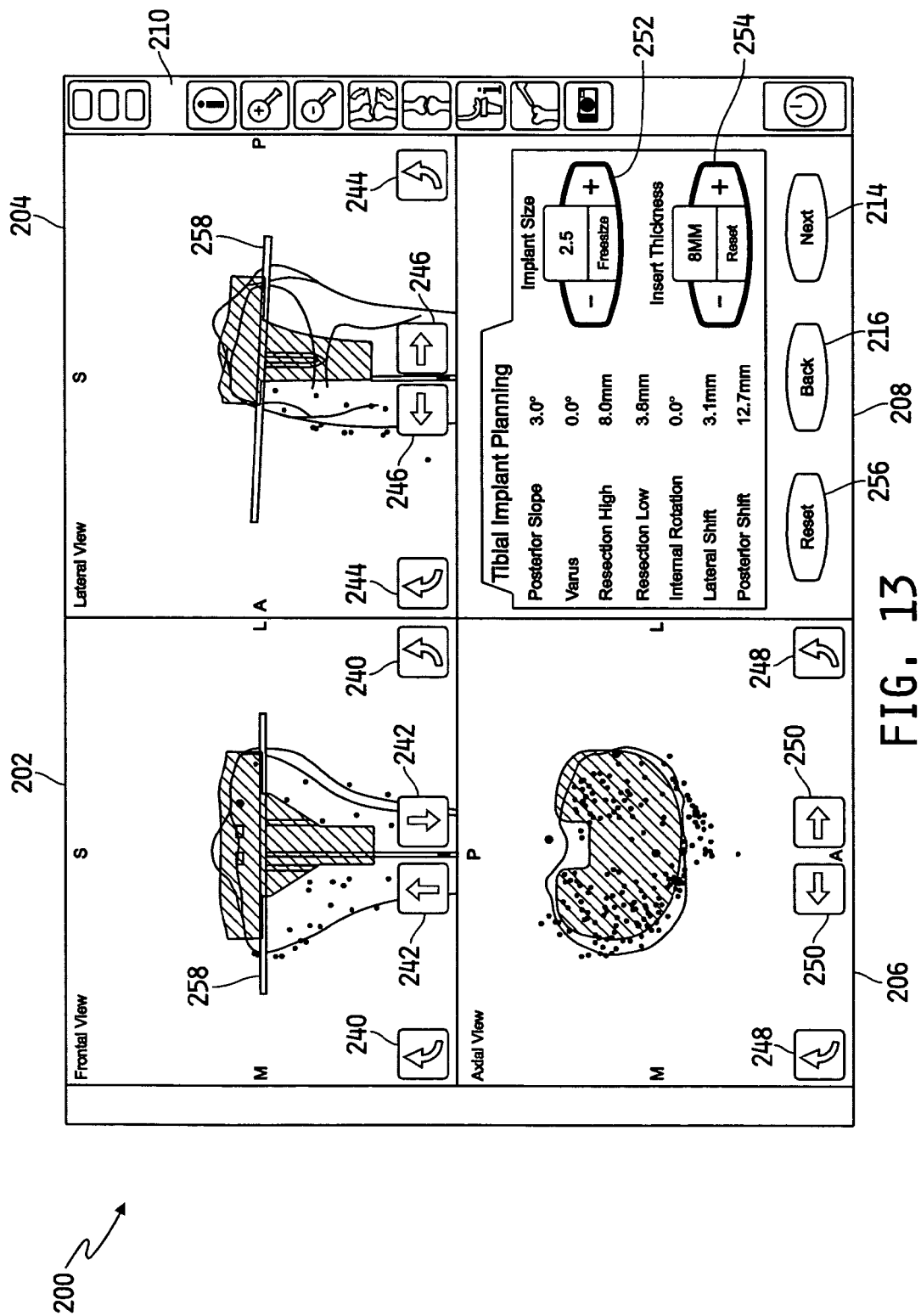

Once the relevant bones (i.e., the proximal tibia and distal femur) have been registered in process step 126, the algorithm 120 advances to process step 138 in which the computer 12 displays images of the individual surgical steps of the orthopaedic surgical procedure and the associated navigation data to the surgeon 50. To do so, the process step 138 includes a number of sub-steps 140-154. In process step 140 the planning for the tibial implant is performed. Typically, the selection of the tibial implant is performed in the process step 124, but may be modified in the process step 140 depending upon how well the selected implant fits with the proximal tibia. As illustrated in FIG. 13, a graphically rendered model of the tibial implant is displayed superimposed over the rendered model of the tibia bone in the navigation panes 202, 204, 206. The positioning of the tibial implant can be adjusted via the selection of a number of implant adjustment buttons. For example, the varus/valgus rotation of the orthopaedic implant may be adjusted via the buttons 240, the superior/inferior or proximal/distal translation of the orthopaedic implant may be adjusted via the buttons 242, the slope of the orthopaedic implant may be adjusted via the buttons 244, the anterior/posterior translation of the orthopaedic implant may be adjust via the buttons 246, the internal/external rotation of the orthopaedic implant may be adjusted by the buttons 248, and the medial/lateral translation of the orthopaedic implant may be adjusted by the buttons 250. Data related to the positioning of the orthopaedic implant is displayed in the surgical step panel 208. Some attributes of the implant, such as the orthopaedic implant size and thickness may be adjusted via the selection of button panels 252 and 254, respectively. Additionally the original location and orientation of the implant may be reset via selection of a reset button 256. Using the various implant adjustment buttons and the implant attribute button panels 252, 254, the surgeon 50 positions and orientates the tibial implant such that a planned resection plane 258 of the tibia bone is determined. Because the surgeon 50 can see a visual rendering of the planned resection plane and the location/orientation of the tibial implant, the surgeon 50 can alter the location and orientation of the resection plane and/or tibial implant until the surgeon 50 is satisfied with the final fitting of the tibial implant to the resected proximal tibia. Once so satisfied, the surgeon 50 may proceed to the next surgical step by selecting the next button select the next button 214.

Figure 14:
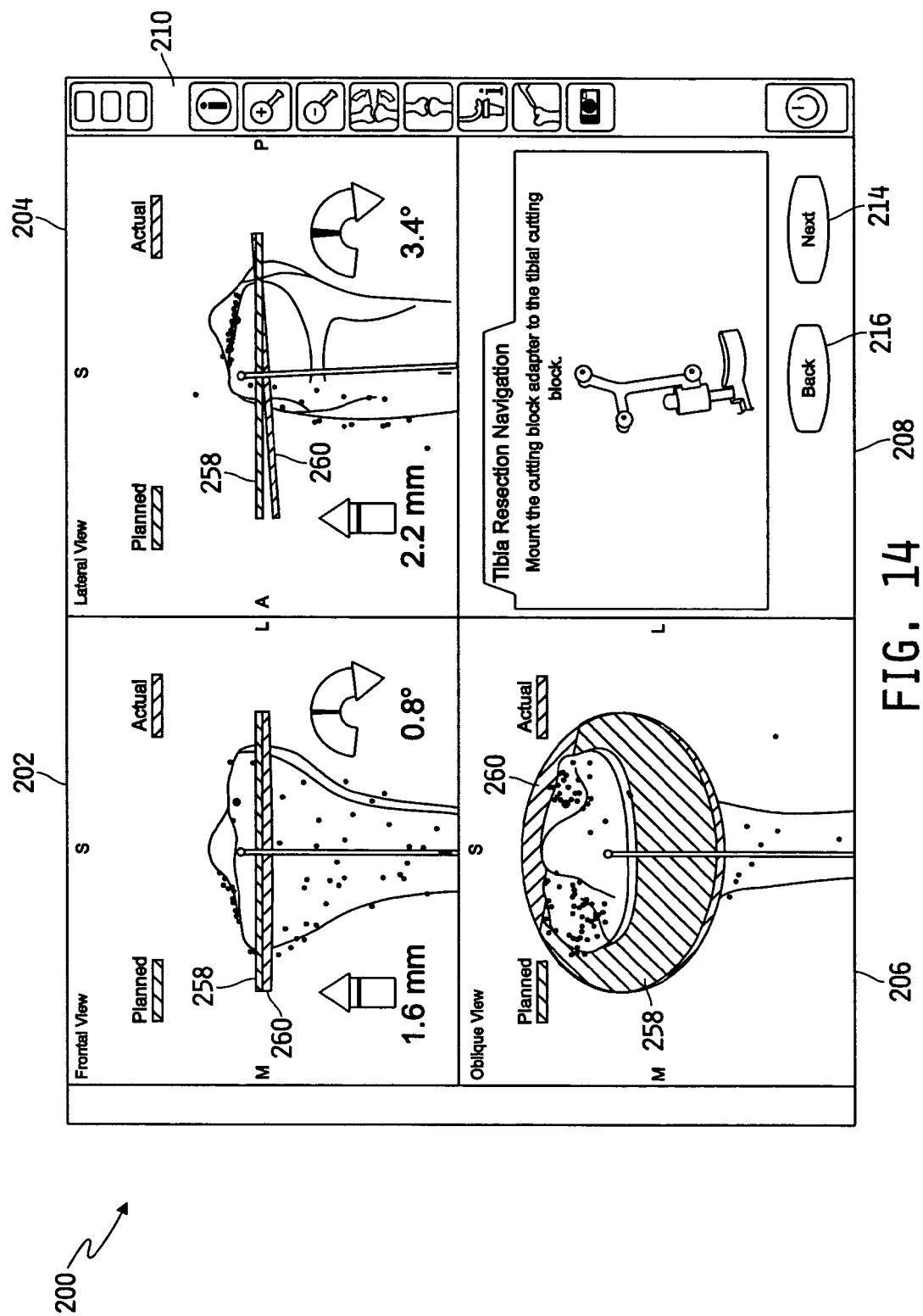

In process step 142 the resectioning of the proximal tibia is planned. To do so, a resection jig, such as the tibial resection jig 90 illustrated in and described above in regard to FIG. 5, is coupled with the tibia bone of the patient 56 near the desired resection location of the proximal tibia. As illustrated in FIG. 14, the computer 12 displays the correct surgical tool to use in the present step in the surgical step pane 208. In response, the computer 20 displays an actual resection plane 260 to the surgeon 50 on the navigation panes 202, 204, 206. As shown, a planned resection plane 258, as determined in step 140, is also displayed. The surgeon 50 may then adjust the coupling of the jig 90 with the tibia bone of the patient 56 such that the actual resection plane 260 overlaps or nearly overlaps the planned resection plane 258. In this way, the surgeon 50 is able to visually monitor the actual resection plane 260 while adjusting the jig 90 such that an accurate resection of the tibia can occur. The surgeon 50 may advance to the next surgical step by selecting the next button 214.

Figure 15:
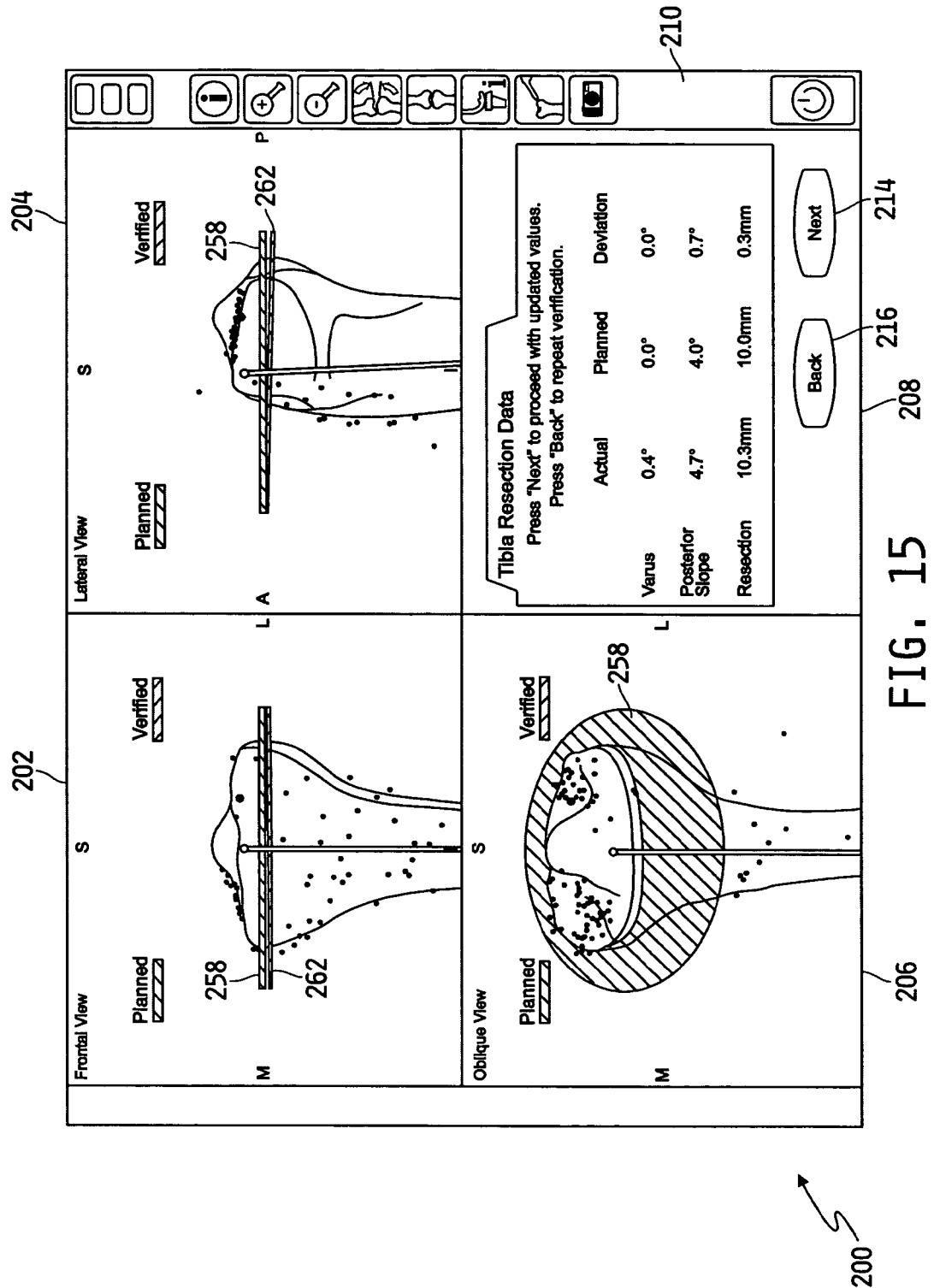

Once the surgeon 50 has reviewed and adjusted the actual resection plane 260 in process step 142, the algorithm 120 advances to process step 144. In process step 144, the tibia is resected using the appropriate resection tool and the jig 90 coupled with the tibia bone of the patient 56. After the proximal tibia has been resected, the computer 12 displays a verified resection plane 262 superimposed with the planned resection plane 258 as illustrated in FIG. 15. The computer 12 also displays data related to the resection of the proximal tibia, including actual, planned, and deviation measurements, in the surgical step panel 208. In this way, the surgeon 50 can compare the final resection of the tibia and the planned resection. If needed, the surgeon 50 can repeat the resectioning process to remove more the proximal tibia. Once the surgeon 50 is satisfied with the resection of the tibia bone, the surgeon 50 may advance to the next surgical step by selecting the next button 214.

Once the tibia bone of the patient 56 has been resected, the relevant distal femur bone is resected in process steps 146-150. In process step 146, the planning for the femoral implant is performed. The femoral implant planning of process step 146 is similar to the tibial implant planning performed in process step 124. During process step 146, the surgeon 50 positions and orients the femoral implant such that a planned resection plane of the distal femur is determined and may also select relevant implant parameters (e.g., size, type, etc.). Because the surgeon 50 can see a visual rendering of the planned resection plane and the location/orientation of the femoral implant, the surgeon 50 can alter the location and orientation of the planned resection plane and/or femoral implant until the surgeon 50 is satisfied with the final fitting of the femoral implant to the resected distal femur.

Once the femoral implant planning is complete, the algorithm 120 advances to process step 148. In process step 148, the resectioning of the distal femur of the patient 56 is planned. The resection planning of the process step 148 is similar to the planning of the tibia resection performed in the process step 142. During the process step 148, a femoral resection jig is coupled with the femur bone of the patient 56. In response, the computer 12 displays an actual resection plane superimposed on the planned resection plane developed in process step 146. By repositioning the femoral resection jig, the surgeon 50 is able to alter the actual resection plane such that an accurate resection of the femur can occur.

Once the surgeon 50 has reviewed and adjusted the actual resection plane of the femur bone, the algorithm 120 advances to process step 150 in which the distal femur is resected using the appropriate resection tool and femoral jig. After the distal femur has been resected, the computer 12 displays a verified resection plane superimposed with the planned resection plane determined in process step 146. In this way, the surgeon 50 can compare the final resection of the femur with the planned resection. Again, if needed, the surgeon 50 can repeat the resectioning process to remove more the distal femur.

Figure 16:
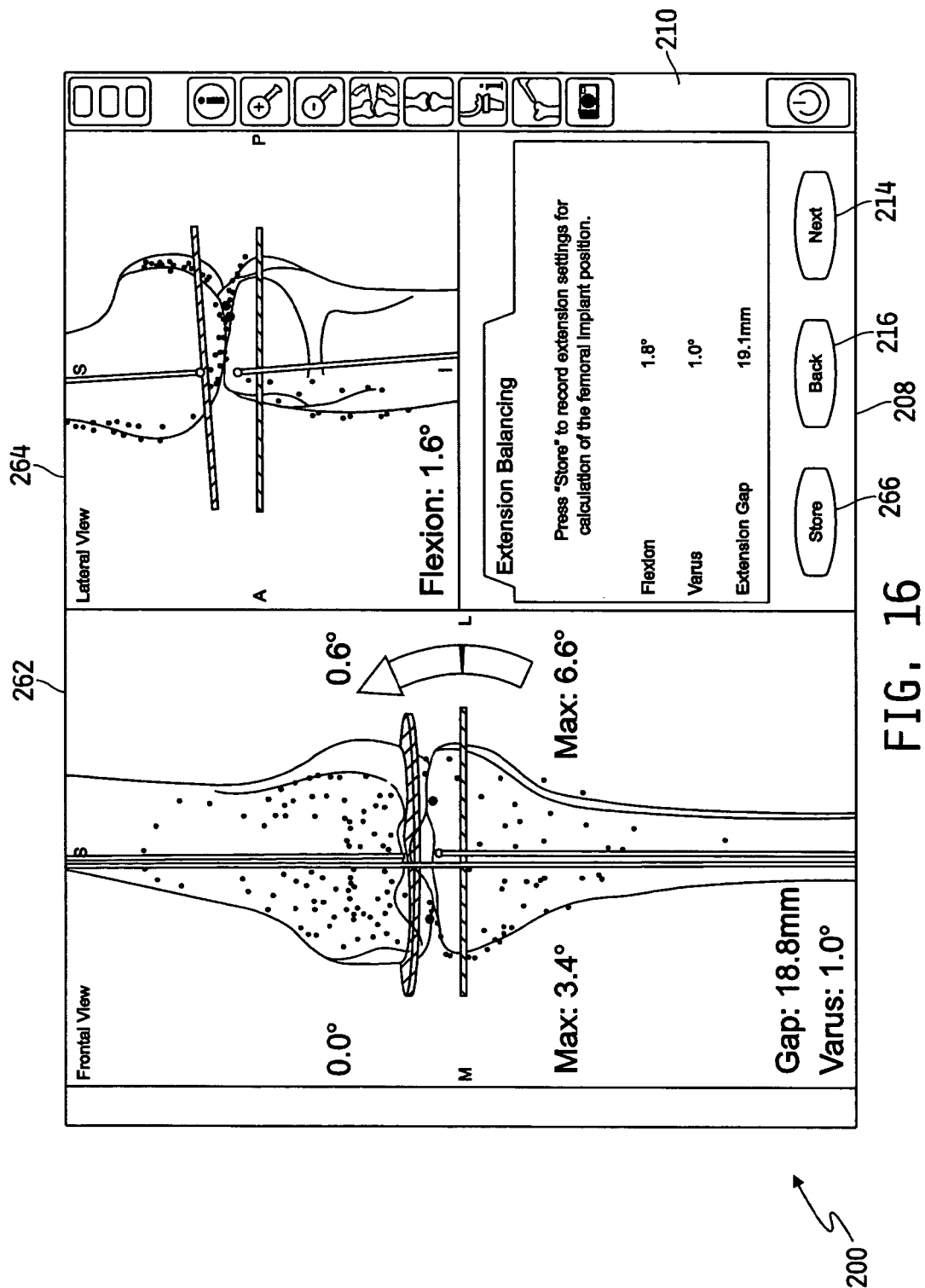

Once the distal femur of the patient 56 has been resected, the algorithm 120 advances to process step 152. In process step 152, ligament balancing of the patient's 56 tibia and femur is performed. Although illustrated as occurring after the resectioning of the tibia and femur bones in FIG. 7, ligament balancing may occur immediately following any resection step (e.g. after the tibia bone is resected) in other embodiments. In process step 152, orthopaedic implant trials (i.e., temporary orthopaedic implants similar to the selected orthopaedic implants) are inserted between the resected ends of the femur and tibia of the patient 56. As illustrated in FIG. 16, the computer 12 displays alignment data of the femur and tibia bone to the surgeon 50 via the display device 44. Specifically, the computer 12 displays a frontal view of the femur bone and tibia bone of the patient 56 in a frontal view pane 262 and a lateral view of the femur and tibia bones in a lateral view pane 264. Each of the panes 262, 264 display alignment data of the femur and tibia bones. Additional alignment data is displayed in the surgical step pane 208. The alignment data may be stored (e.g., in a data storage device included in the computer 20) by selection of a store button 266. The alignment data may subsequently be retrieved and reviewed or used in another procedure at a later time.

Ligament balancing is performed to ensure a generally rectangular shaped extension gap and a generally rectangular shaped flexion gap at a predetermined joint force value has been established between the patient's 56 proximal tibia and the distal femur. To do so, a ligament balancer may be used to measure the medial and lateral joint forces and the medial and lateral gap distances when the patient's 56 leg is in extension (i.e., the patient's 56 tibia is positioned at about 0 degrees relative to the patient's femur) and in flexion (i.e., the patient's 56 tibia is positioned at about 90 degrees relative to the patient's femur). An exemplary ligament balancer that may be used to perform these measurements is described in U.S. patent application Ser. No. 11/094,956, filed on Mar. 31, 2005, the entirety of which is expressly incorporated herein by reference. In either extension or flexion, if the medial and lateral gap distances are not approximately equal (i.e., do not form a generally rectangular shaped joint gap) at the predetermined joint force value, ligament release (i.e., cutting of a ligament) may be performed to equalize the medial and/or lateral gap distances. Additionally or alternatively, the orthopaedic implant trial may be replaced with an alternative implant trial. In this way, the surgeon 50 ensures an accurate alignment of the tibia bone and femur bone of the patient 56.

Figure 17:
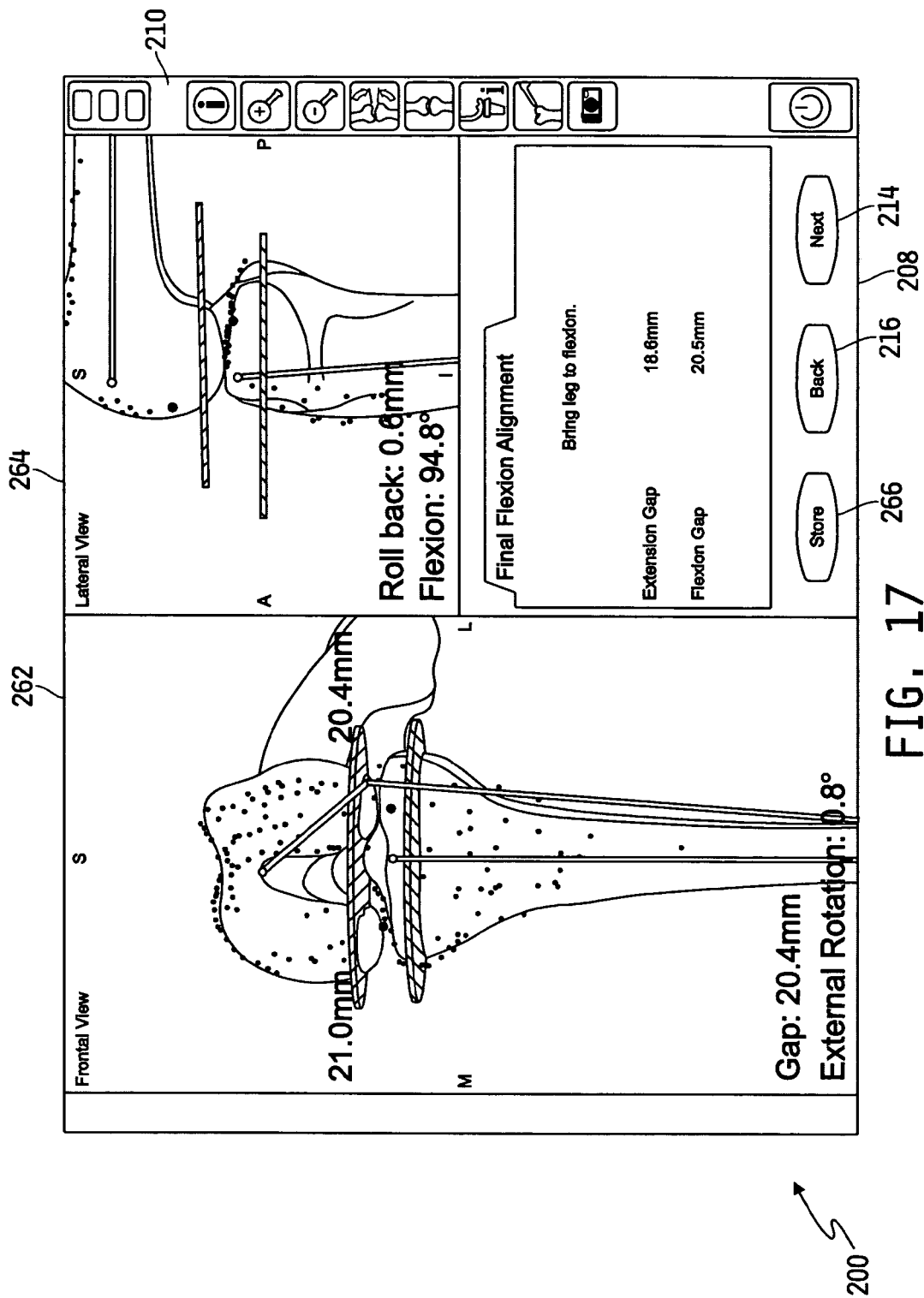

Once any desired ligament balancing is completed in process step 152, the algorithm 120 advances to process step 154 in which a final verification of the orthopaedic implants is performed. In process step 154, the orthopaedic implants are coupled with the distal femur and proximal tibia of the patient 56 and the alignment of the femur and tibia bones are verified in flexion and extension. To do so, the computer 12 displays the rendered images of the femur bone and tibia bone and alignment data to the surgeon 50 via the display device 44, as illustrated in FIG. 17. As indicated in the surgical step pane 208, the surgeon 50 is instructed to move the patient's 56 leg to flexion and extension such that the overall alignment can be determined and reviewed. If the femur and tibia bones of the patent 56 are not aligning (i.e., the flexion and/or extension gap is non-rectangular) to the satisfaction of the surgeon 50, the surgeon may perform additional ligament balancing as discussed above in regard to process step 152. Once the surgeon 50 has verified the final alignment of the femur and tibia bones (i.e., the flexion and extension gaps), the surgeon 50 may store the final alignment data via selecting the store button 266. The surgeon 50 may subsequently complete the orthopaedic surgical procedure by selecting the next button 214.

Figure 18:
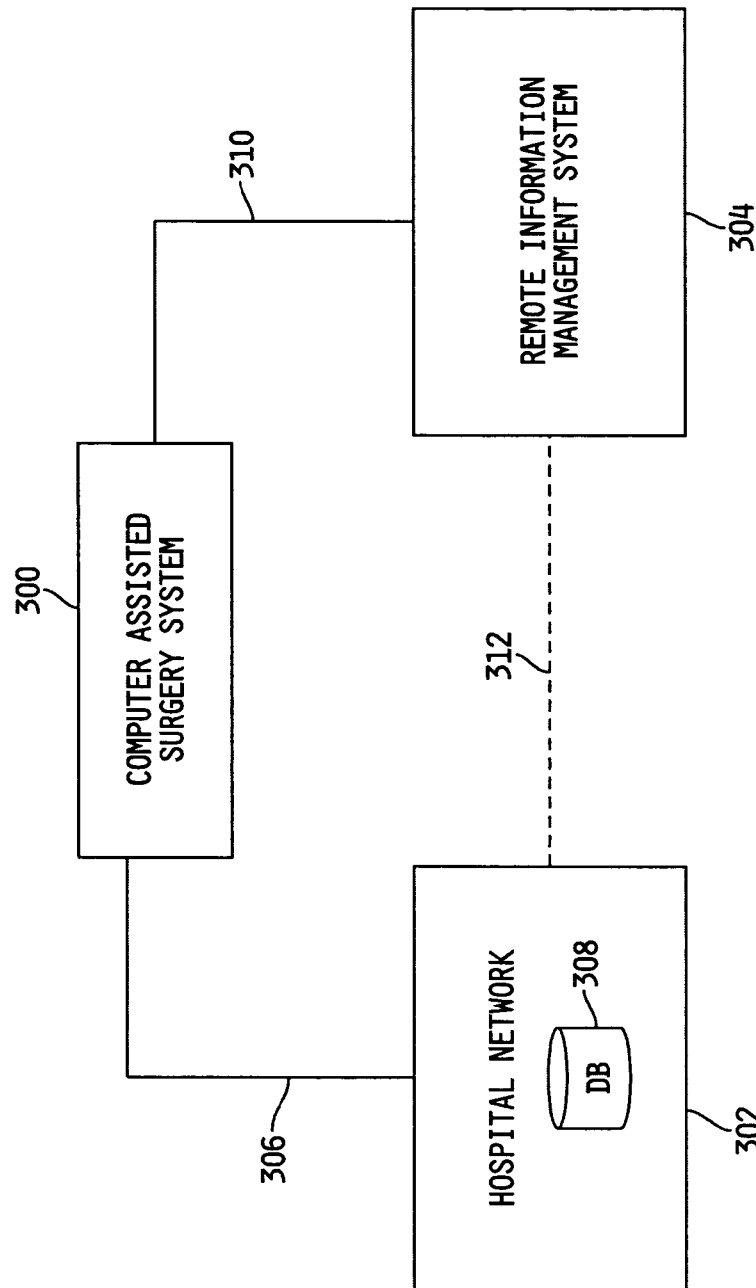
FIG. 18 is a simplified block diagram of another CAOS system.

Referring now to FIG. 18, in another embodiment, a computer assisted surgery (CAOS) system 300 for assisting a surgeon in the performance of an orthopaedic surgical procedure is configured to communicate with a hospital network 302 and/or a remote information management system 304. The hospital network 302 may be embodied as any type of data network of a hospital or other healthcare facility and may include any number of remote computers, communication links, server machines, client machines, databases 308, and the like. The remote information management system 304 may be embodied as any type of remote computer, remote computer system, or network of remote computers. For example, the system 304 may be embodied as a computer located in the offices of the surgeon performing the orthopaedic surgical procedure. As such, the term "remote computer", as used herein, is intended to refer to any computer or computer system that is not physically located in the operating room wherein the orthopaedic surgical procedure is to be performed. That is, a remote computer may form a portion of the remote information management system 304 or the hospital network 302.

The CAOS system 300 is communicatively coupled with the hospital network 302 via a communication link 306. The CAOS system 300 may transmit data to and/or receive data from the hospital network 302 via the communication link 306. The CAOS system 300 is also communicatively coupled with the remote information management system 304 via a communication link 310. The CAOS system 300 may transmit/receive data from the remote information manage system 304 via the communication link 310. Additionally, in some embodiments, the remote information management system 304 may be communicatively coupled with the hospital network 302 via a communication link 312. In such embodiments, the remote management information system 304 and the hospital network 302 may transmit and/or receive data from each other via the communication link 312. The communication links 306, 310, 312, may be wired or wireless communication links or a combination thereof. The CAOS system 300, the hospital network 302, and the remote information management system 304 may communicate with each other using any suitable communication technology and/or protocol including, but not limited to, Ethernet, USB, TCP/IP, Bluetooth, ZigBee, Wi-Fi, Wireless USB, and the like. Additionally, any one or more of the communication links 306, 310, 312, may form a portion of a larger network including, for example, a publicly-accessible global network such as the Internet.

In use, the surgeon may operate the computer assisted orthopaedic surgery system 300 to retrieve pre-operative data from the remote information management system 304 via the communication link 310. As used herein, the term "pre-operative data" refers to any data related to the orthopaedic surgical procedure to be performed, any data related to the patient on which the orthopaedic surgical procedure will be performed, or any other data useful to the surgeon that is generated prior to the performance of the orthopaedic surgical procedure. For example, the pre-operative data may include, but is not limited to, the type of orthopaedic surgical procedure that will be performed, the type of orthopaedic implant that will used, the anticipated surgical procedure steps and order thereof, rendered images of the relevant anatomical portions of the patient, digital templates of the orthopaedic implants and/or planned resection lines and the like, pre-operative notes, diagrams, surgical plans, historic patient data, X-rays, medical images, medical records, and/or any other data useful to the surgeon during the performance of the orthopaedic surgical procedure.

Additionally, the surgeon may operate the CAOS system 300 to retrieve patient-related data from the hospital network 302 via the communication link 306. As used herein, the term "patient-related data" refers to any data related to the patient on whom the orthopaedic surgical procedure will be performed including, but not limited to, patient medical records, X-rays, patient identification data, or the like. In some embodiments, the CAOS system 300 may also retrieve procedure-related data, such as the names of other surgeons that have performed similar orthopaedic surgical procedures, statistical data related to the hospital and/or type of orthopaedic surgical procedure that will be performed, and the like, from the hospital network 302.

The pre-operative data may be generated, developed, or otherwise collected by the surgeon via the remote information management system 304. For example, the surgeon may use a computer located at the surgeon's office (which is typically located away from the hospital or other healthcare facility in which the orthopaedic surgical procedure is to be performed) to determine the selection of surgical steps that will be performed during the orthopaedic surgical procedure. In some embodiments, the surgeon may operate the system 304 to retrieve patient-related data, such as patient medical history or X-rays, and/or procedure-related data from the hospital network 302. The surgeon may then use the patient-related/procedure-related data retrieved from the network 302 in the process of developing or generating the pre-operative data. For example, using the system 304, the surgeon may develop pre-operative data, such as the type of orthopaedic implant that will be used, based on X-rays of the patient retrieved from the network 302. Additionally, in some embodiments, the surgeon may store the pre-operative data and/or other data on a removable memory device or the like as discussed in more detail below in regard to FIG. 19.

Once the pre-operative data has been generated, the surgeon may save the pre-operative data on the hospital network 302, for example in the database 308, by transmitting the pre-operative data to the network 302 via the communication link 312. Additionally, the surgeon may subsequently operate the computer assisted surgery system 300 to retrieve the pre-operative data from the system 304 and/or patient-related/procedure related data from the network 302. As discussed in more detail below in regard to FIGS. 19 and 20a-b, the CAOS system 300 may be configured to use the pre-operative data and/or patient-related data during the performance of the orthopaedic surgical procedure. The surgeon may also operate the CAOS system 300 to store data on the hospital network 302 (e.g., in the database 308) during or after the orthopaedic surgical procedure. For example, the surgeon may dictate or otherwise provide surgical notes during the procedure, which may be recorded and subsequently stored in the database 308 of the network 302 via the link 306.

Figure 19:
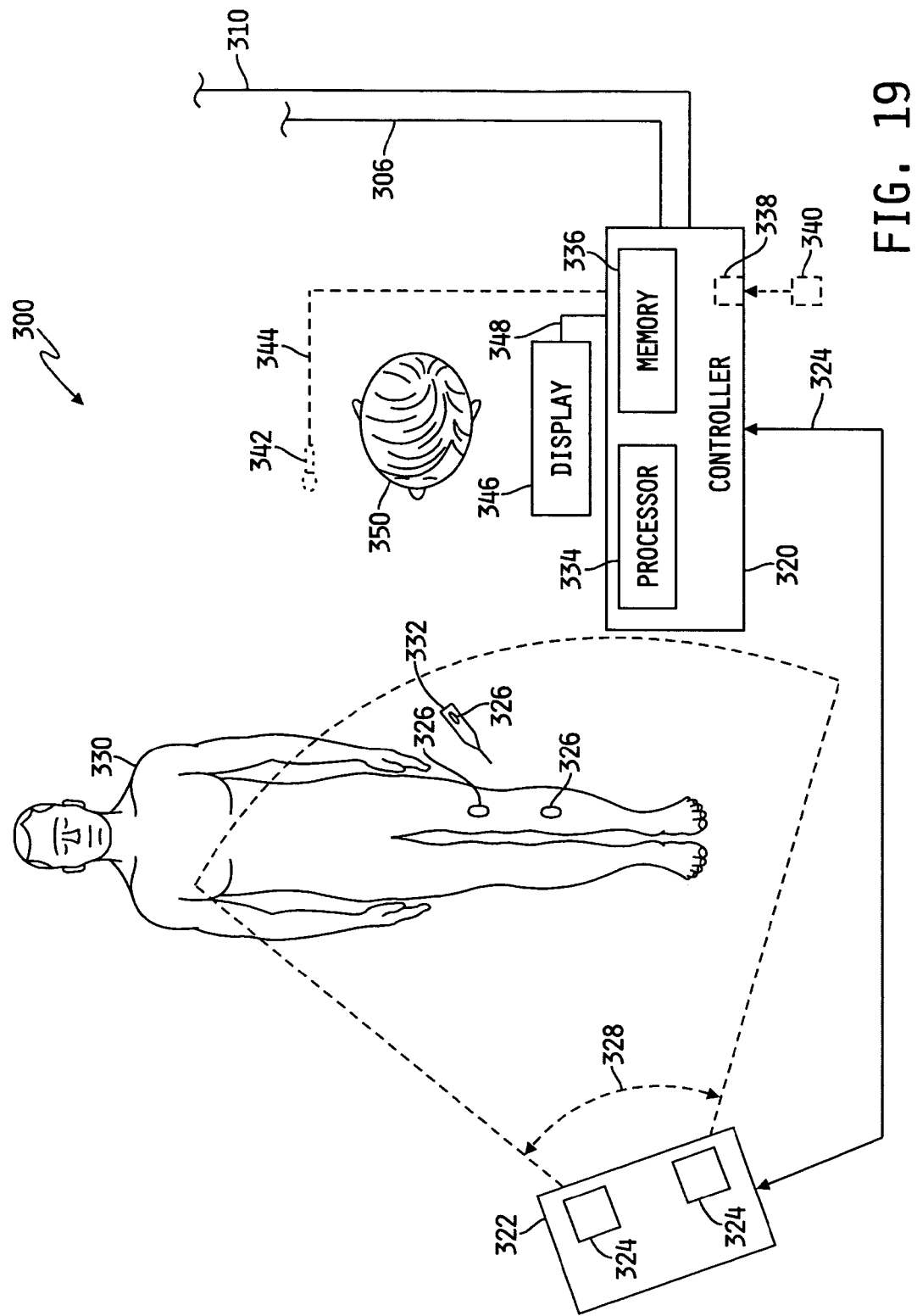
FIG. 19 is a simplified diagram of the CAOS system of FIG. 19.

Referring now to FIG. 19, the CAOS system 300 includes a controller 320 and a camera unit 322. The controller 320 is communicatively coupled with the camera unit 322 via a communication link 324. The communication link 324 may be any type of communication link capable of transmitting data (i.e., image data) from the camera unit 322 to the controller 320. For example, the communication link 324 may be a wired or wireless communication link and use any suitable communication technology and/or protocol to transmit the image data. In the illustrative embodiment, the camera unit 322 is similar to the camera unit 16 of the system 10 described above in regard to FIG. 1. The camera unit 322 includes cameras 324 and may be used in cooperation with the controller 320 to determine the location of a number of sensors 326 positioned in a field of view 328 of the camera unit 322. In the illustrative embodiment, the sensors 326 are similar to the sensor arrays 54, 62, 82, 96 described above in regard to FIGS. 2, 3, 4, and 5, respectively. That is, the sensors 326 may include a number of reflective elements and may be coupled with bones of a patient 330 and/or various medical devices 332 used during the orthopaedic surgical procedure. Alternatively, in some embodiments, the camera unit 322 may be replaced or supplemented with a wireless receiver (which may be included in the controller 320 in some embodiments) and the sensors 326 may be embodied as wireless transmitters. Additionally, the medical devices 332 may be embodied as "smart" medical devices such as, for example, smart surgical instruments, smart surgical trials, smart surgical implants, and the like. In such embodiments, the controller 320 is configured to determine the location of the sensors 326 (i.e., the location of the bones and/or the medical devices 332 with which the sensors 326 are coupled) based on wireless data signals received from the sensors 326.

The controller 320 is also communicatively coupled with a display device 346 via a communication link 348. Although illustrated in FIG. 19 as separate from the controller 320, the display device 346 may form a portion of the controller 320 in some embodiments. Additionally, in some embodiments, the display device 346 may be positioned away from the controller 320. For example, the display device 346 may be coupled with a ceiling or wall of the operating room wherein the orthopaedic surgical procedure is to be performed. Additionally or alternatively, the display device 346 may be embodied as a virtual display such as a holographic display, a body mounted display such as a heads-up display, or the like. The controller 320 may also be coupled with a number of input devices such as a keyboard and/or a mouse. However, in the illustrative embodiment, the display device 346 is a touch-screen display device capable of receiving inputs from a surgeon 350. That is, the surgeon 350 can provide input data to the display device 346 and controller 320, such as making a selection from a number of on-screen choices, by simply touching the screen of the display device 346.

The controller 320 may be embodied as any type of controller including, but not limited to, a personal computer, a specialized microcontroller device, or the like. The controller 320 includes a processor 334 and a memory device 336. The processor 334 may be embodied as any type of processor including, but not limited to, discrete processing circuitry and/or integrated circuitry such as a microprocessor, a microcontroller, and/or or an application specific integrated circuit (ASIC). The memory device 336 may include any number of memory devices and any type of memory such as random access memory (RAM) and/or read-only memory (ROM). Although not shown in FIG. 19, the controller 320 may also include other circuitry commonly found in a computer system. For example, the controller 320 also includes input/output circuitry to allow the controller 320 to properly communicate with the hospital network 302 and the remote information management system 304 via the communication links 306 and 310.

In some embodiments, the controller 320 may also include a peripheral port 338 configured to receive a removable memory device 340. In the illustrative embodiment, the peripheral port 338 is a Universal Serial Bus (USB) port. However, in other embodiments, the peripheral port 338 may be embodied as any type of serial port, parallel port, or other data port capable of communicating with and receiving data from the removable memory device 340. The removable memory device 340 may be embodied as any portable memory device configured for the purpose of transporting data from one computer system to another computer system. In some embodiments, the removable memory device 340 is embodied as a removable solid-state memory device such as a removable flash memory device. For example, the removable memory device 340 may be embodied as a "memory stick" flash memory device, a SmartMedia™ flash memory device, or a CompactFlash™ flash memory device. Alternatively, in other embodiments, the removable memory device 340 may be embodied as a memory device having a microdrive for data storage. Regardless, the removable memory device 340 is capable of storing data such as pre-operative data for later retrieval.

Additionally, in some embodiments, the CAOS system 300 may include a microphone 342 communicatively coupled with the controller 320 via a communication link 344. The microphone 342 may be any type of microphone or other receiving device capable of receiving voice commands from a surgeon 350. The microphone 342 may be wired (i.e., the communication link 344 is a wired communication link) or wireless (i.e., the communication link 344 is a wireless communication link). The microphone 342 may be attached to a support structure, such as a ceiling or wall of the operating room, so as to be positionable over the surgical area. Alternatively, the microphone 342 may be appropriately sized and configured to be worn, such as on the surgeon's 350 head or clothing, or held by the surgeon 350 or other surgical staff member. For example, in some embodiments, the microphone 342 is an ear or throat microphone. As such, the term microphone, as used herein, is intended to include any transducer device capable of transducing an audible sound into an electrical signal.

In use, the surgeon 350 may operate the controller 320 to retrieve pre-operative data from the remote information management system 304 (e.g., from a surgeon's computer located in the surgeon's office) via communication link 310 prior to the performance of the orthopaedic surgical procedure. Additionally or alternatively, the surgeon 350 may operate the controller 320 to retrieve pre-operative data, patient-related data, and/or procedure-related data from the hospital network prior to the orthopaedic surgical procedure. In embodiments wherein the controller 320 includes a peripheral port 338, the surgeon 350 may operate the controller 320 to retrieve data (e.g., pre-operative data, patient-related data, and/or procedure-related data) from the removable memory device 340. Based on the retrieved data, the controller 320 is configured to determine a workflow plan of the orthopaedic surgical procedure and control the display device 346 to display images of the individual surgical steps which form the orthopaedic surgical procedure according to the workflow plan. As used herein, the term "workflow plan" is intended to refer to an ordered selection of instructional images that depict individual surgical steps that make up at least a portion of the orthopaedic surgical procedure that is to be performed. The instructional images may be embodied, for example, as images of surgical tools and associated text information, graphically rendered images of surgical tools and relevant patient anatomy, or the like. The instructional images are stored in an electronic library, which may be embodied as, for example, a database, a file folder or storage location containing separate instructional images and an associated "look-up" table, hard-coded information stored in the memory device 336, or in any other suitable electronic storage. Accordingly, a workflow plan may be embodied, for example, as an ordered selection of instructional images that are displayed to the surgeon 350 via the display device 346 such that the instructional images provide a surgical "walk-through" of the procedure or portion thereof. Alternatively, a workflow plan may include a number of surgical sub-step images, some of which may or may not be displayed to and performed by the surgeon 350 based on selections chosen by the surgeon 350 during the performance of the orthopaedic surgical procedure.

The controller 320 also cooperates with the camera head 322 and display unit 346 to determine and display the location of the sensors 326 and structures coupled with such sensors (e.g., bones of the patient, medical devices 332, etc.). Additionally, the surgeon 350 may operate the controller 320 to display portions of the pre-operative data, patient-related data, and/or procedure-related data on the display device 346. To do so, the controller 320 may retrieve additional data from the network 302 and/or system 304. Further, during the performance of the orthopaedic surgical procedure, the controller 320 may be configured to determine deviations of the surgeon 350 from the determined workflow plan and record such deviations. Additionally, the controller 320 may be configured to record the selections made by the surgeon and screenshots of the images displayed to the surgeon 350 during the performance of the orthopaedic surgical procedure. The controller 320 may also record surgical notes provided by surgeon 350. In embodiments including the microphone 342, the surgeon 350 may provide verbal surgical notes to the controller 350 for recording. Alternatively, the surgeon 350 may provide the surgical notes to the controller 320 via other input means such as a wired or wireless keyboard, a touch-screen keyboard, or via the removable memory device 340.

Once the orthopaedic surgical procedure is complete, the controller 320 may be configured to store surgical data on the hospital network 302 (e.g., in the database 308) via the communication link 306. The surgical data may include, but is not limited to, the pre-operative data, the patient-related data, the procedure-specific data, deviation data indicative of the deviations of the surgeon 350 from the workflow plan, verbal or other surgical notes, data indicative of selections made by the surgeon 350 during the procedure, and/or screenshots of images displayed to the surgeon 350 during the performance of the orthopaedic surgical procedure.

Figure 20A:
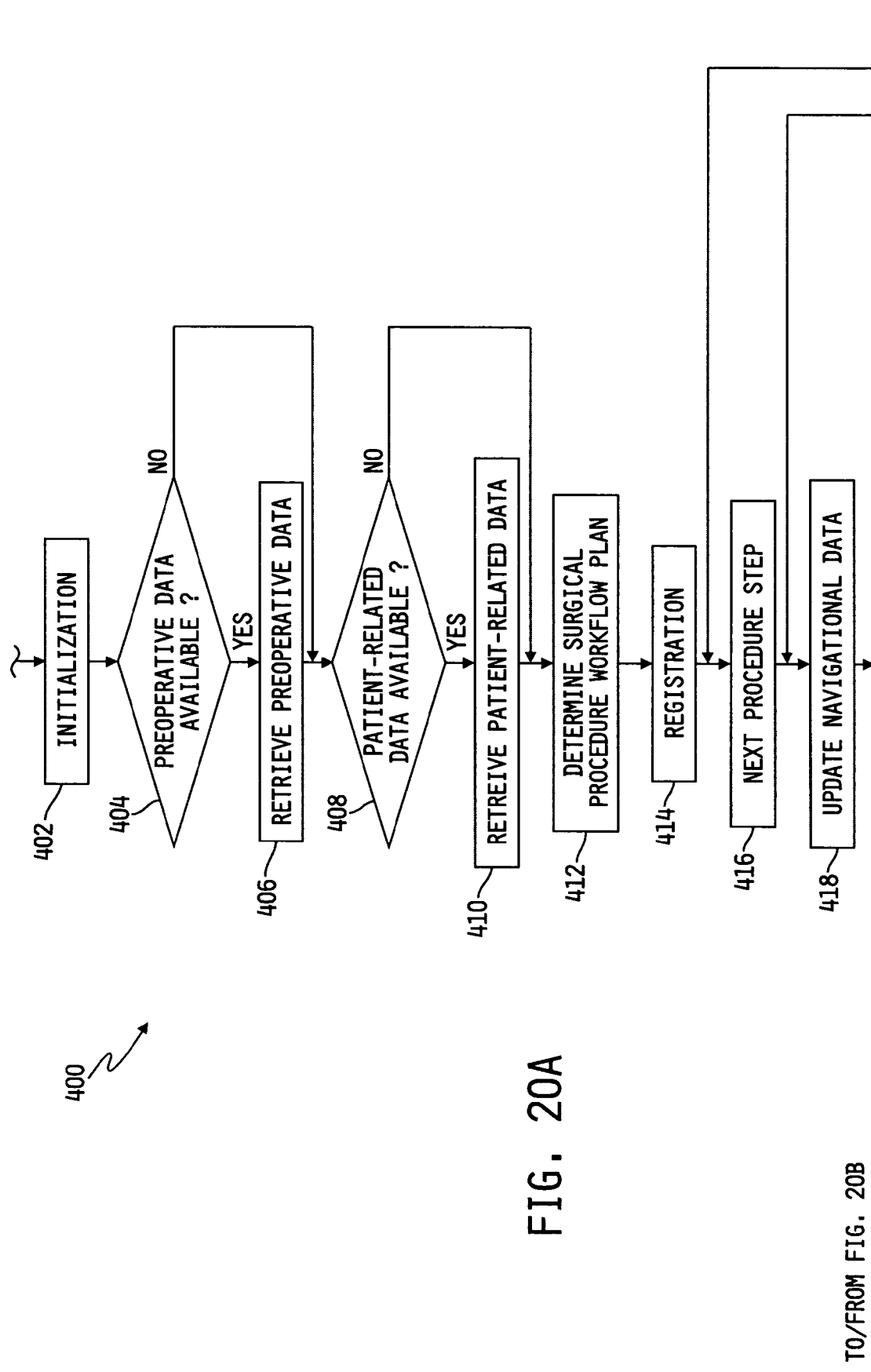
FIGS. 20a-20b each show a simplified flowchart diagram of an algorithm for operating a computer assisted orthopaedic surgery system, which may be used with the CAOS system of FIG. 18.
Figure 20B:
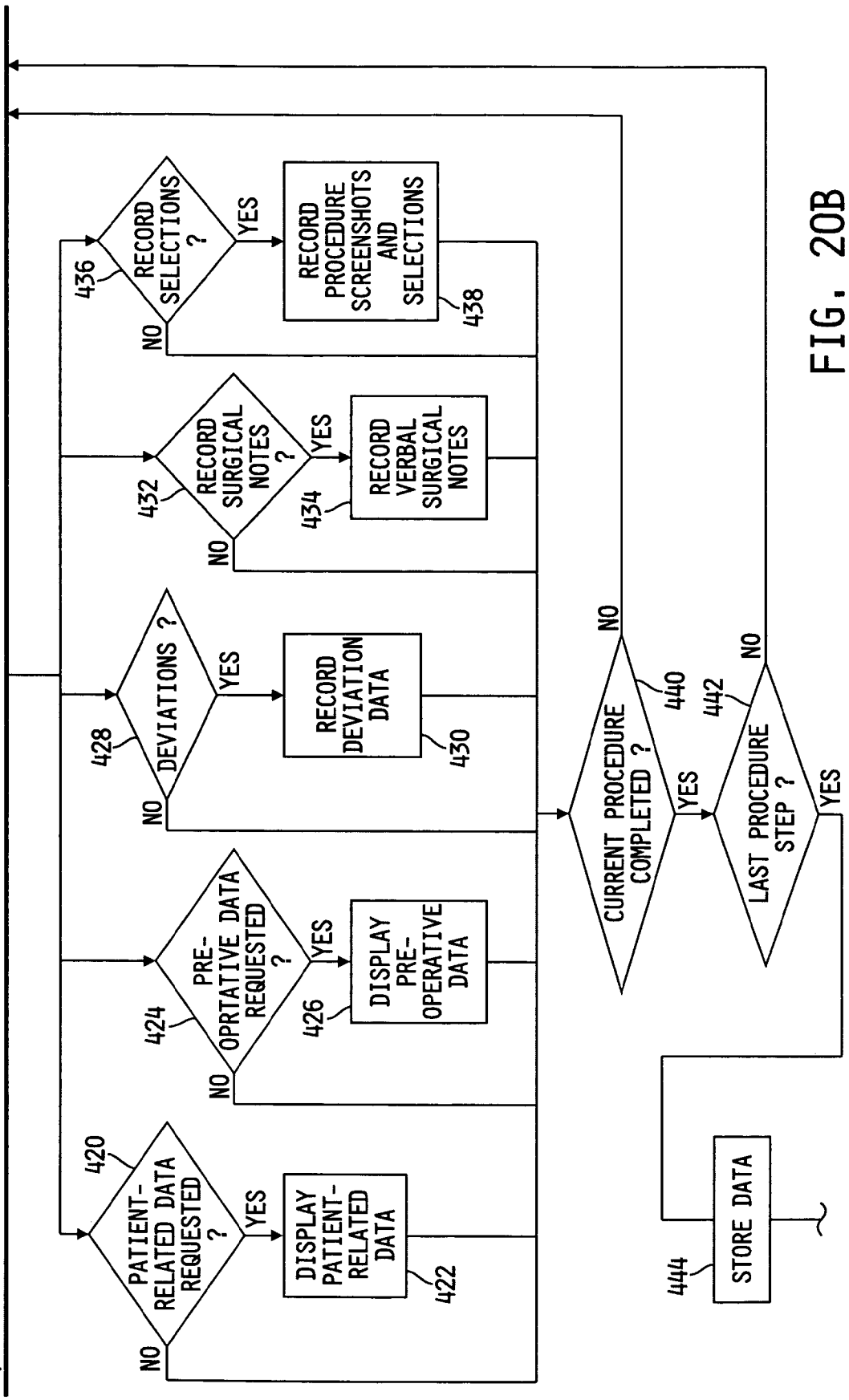

Referring now to FIGS. 20a-b, an algorithm 400 for assisting a surgeon in performing an orthopaedic surgical procedure may be executed by the CAOS system 300. The algorithm 400 may be embodied as a software program stored in the memory device 336 and executed by the processor 334 of the controller 320. The algorithm 400 begins with process step 402 in which the CAOS system 300 is initialized. During process step 402, the settings and preferences, such as the video settings of the display device 334, of the system 300 may be selected. Additionally, devices of the system 300, such as the camera head 322 and the touch screen of the display device 346, may be calibrated.

In process step 404, the controller 320 determines if any pre-operative data is available. If so, the pre-operative data is retrieved in process step 406. To do so, the surgeon 350 may operate the controller 320 to retrieve the pre-operative data from the remote information management system 304 via the communication link 310, from the hospital network 302 via communication link 306, and/or from the removable memory device 340. Alternatively, in some embodiments, the controller 320 may be configured to automatically check the system 304, network 302, and/or memory device 340 to determine if pre-operative data is available and, if so, to automatically retrieve such data. If pre-operative data is not available or if the surgeon 350 instructs the controller 320 to not retrieve the pre-operative data, the algorithm 400 advances to the process step 408 in which the controller 320 determines if any patient-related data is available. If so, the patient-related data is retrieved in process step 410. The patient-related data may be retrieved from the hospital network 302, the remote system 304, and/or the removable memory device 340. The controller 320 may retrieve the patient-related data automatically or may be operated by the surgeon 350 to retrieve the patient-related data. If patient-related data is not available or if the surgeon 350 instructs the controller 320 to not retrieve the patient-related data, the algorithm 400 advances to process step 412.

In process step 412, the controller 320 determines the workflow plan of the orthopaedic surgical procedure. To do so, the controller 320 may determine the workflow plan based on a portion of the pre-operative data and/or the patient-related data. That is, the controller 320 determines an ordered selection of instructional images based on the pre-operative data. The instructional images may be retrieved from an electronic library of instructional images such as a database or image folder. The instructional images are selected so as to provide a surgical "walk-through" of the orthopaedic surgical procedure based on the prior decisions and selections of the surgeon (i.e., the pre-operative data). For example, the pre-operative data may include the type of orthopaedic surgical procedure that will be performed (e.g., a total knee arthroplasty procedure), the type of orthopaedic implant that will be used (e.g., make, model, size fixation type, etc.), and the order of the procedure (e.g., tibia first or femur first). Based on this pre-operative data, the controller 320 determines a workflow plan for performing the chosen orthopedic surgical procedure in the order selected and using the chosen orthopedic implant. Because the controller 320 determines the workflow plan based on the pre-operative data, the surgeon 350 is not required to step through a number of selection screens at the time during which the orthopaedic surgical procedure is performed. Additionally, if the pre-operative data includes digital templates of the implants and/or planned resection lines, the controller 320 may use such data to display rendered images of the resulting bone structure of the planned resection and/or the location and orientation of the orthopaedic implant based on the digital template. Accordingly, it should be appreciated that the controller 320 is configured to determine a workflow plan for the chosen orthopaedic surgical procedure based on decisions and selections of the surgeon 350 chosen prior to the performance of the orthopaedic surgical procedure.

In process step 414, the relevant bones of the patient are registered. The registration process of step 414 is substantially similar to the registration process of step 106 of algorithm 100 illustrated in and described above in regard to FIG. 6. That is, a number of sensors 332, which may be embodied as reflective elements in embodiments including camera head 322 or as transmitters in embodiments using "smart" sensors and medical devices, are coupled with the relevant bones of the patient. These bones are subsequently initially registered. The contours and areas of interest of the bones may then be registered using a registration tool such as, for example, the registration tool 80. Based on the registered portions of the bones, the controller 320 determines the remaining un-registered portions and displays graphically rendered images of the bones to the surgeon 350 via the display device 346. The orientation and location of the bones are determined and displayed based on the location data determined based on the images received from the camera unit 322 and the associated sensors 332 (or from the data wirelessly transmitted by the sensors 332). Alternatively, in some embodiments, the relevant bones of the patient may be registered pre-operatively. In such embodiments, the registration data generated during the pre-operative registration process may be retrieved in the process step 414 and used by the controller 320 in lieu of manual registration.

In process step 416, the controller 320 displays the next surgical step of the orthopaedic surgical procedure (i.e., the first surgical step in the first iteration of the algorithm 400) based on the workflow plan determined in process step 312. To do so, the controller 320 may display an image or images to the surgeon 350 via the display device 346 illustrating the next surgical step that should be performed and, in some embodiments, the medical device(s) that should be used. The surgeon 350 can perform the step and advance to the next procedure step or may skip the current procedure step, as discussed below in regard to process step 440. Subsequently, in process step 418, the navigational data is updated. That is, the location and orientation of the relevant bones as determined by the sensors 326 coupled therewith and any medical devices 332 is updated. To do so, the controller 320 receives image data from the camera unit 322 and determines the location of the sensors 326 (i.e., the location of the bones and medical devices 332) based thereon. In embodiments wherein the controller 320 is coupled with or includes a receiver instead of the camera unit 322, the controller 320 is configured to receive location data from the sensors 326, via transmitters included therewith, and determine the location of the sensors 326 based on the location data. Regardless, the controller 320 updates the location and orientation of the displayed bones and/or medical devices 332 based on the received image data and/or location data.

Once the navigational data has been updated in process step 418, a number of process steps 420, 424, 428, 432, and 436 are contemporaneously executed. In process step 420, the controller 320 determines if the surgeon 350 has requested any patient-related data. The surgeon 350 may request data by, for example, selecting an appropriate button on the touch-screen of the display device 346. If so, the requested patient-related data is displayed to the surgeon 350 via the display device 346 in process step 422. If the requested patient-related data is not included in the patient-related data that was retrieved in process step 410, the controller 320 retrieves the requested data from the hospital network 302, the remote information management system 304, and/or the removable memory device 338. In this way, the surgeon 350 can quickly "call up" patient-related data such as X-rays and medical history to review during the orthopaedic surgical procedure. If patient-related data is not requested by the surgeon 350 in process step 420 or after the requested patient-related data has been displayed to the surgeon 350, the algorithm 400 advances to process step 440 described below.

In process step 424, the controller 320 determines if the surgeon 350 has requested any pre-operative data by, for example, selecting an appropriate button on the display device 346. If so, the requested pre-operative data is displayed to the surgeon 340 via the display device 346 in process step 426. If the requested pre-operative data is not included in pre-operative data that was retrieved in process step 404, the controller 320 retrieves the requested data from the remote information management system 304, the hospital network 302, and/or the removable memory device 340. In this way, the surgeon 350 can quickly review any pre-operative data such as surgical notes, diagrams, or images during the orthopaedic surgical procedure. If pre-operative data is not requested by the surgeon 350 in process step 424 or after the requested pre-operative data has been displayed to the surgeon 350, the algorithm 400 advances to process step 440 described below.

In process step 428, the controller 320 determines if the surgeon 350 has deviated from the workflow plan determined in the process step 412. For example, the controller 320 may determine if the surgeon 350 has skipped a surgical procedure step of the orthopaedic surgical procedure, deviated from a planned resection line, used an alternative surgical instrument (based on, for example, the configuration of the sensor array coupled with the instrument), used an alternative orthopaedic implant (based on, for example, an implant identifier scanned during the procedure) or the like. If the controller 320 determines that the surgeon 350 has deviated from the determined workflow plan, the controller 320 records the deviation in the process step 430. The controller 320 may record the deviation by, for example, storing data indicative of the deviation (e.g., error report, screenshots, or the like) in the memory device 336 and/or the removable memory device 340. If the controller 320 determines that the surgeon 350 has not deviated from the workflow plan in process step 428 or after the recent deviation has been recorded in process step 430, the algorithm 400 advances to process step 440 described below. In some embodiments, the surgeon 350 may select whether or not the controller 320 monitors for deviations from the determined workflow plan. If the surgeon 350 requests that deviations not be monitored, the algorithm 400 may skip the process steps 428, 430.

In process step 432, the controller 320 determines if the surgeon 350 has requested the recording of surgical notes. The surgeon 350 may request the recording of surgical notes by, for example, selecting an appropriate button on the touch-screen of the display device 346. If so, the controller 320 records any surgical notes provided by the surgeon 350 in the process step 434. The surgical notes may be embodied as text data that is typed by the surgeon 350 via, for example, a touch controlled keyboard displayed on the display device 346. Alternatively, in embodiments including the microphone 342, the surgical notes may be embodied as voice communication. Additionally, in such embodiments, the controller 320 may be configured to automatically begin recording upon receiving any verbal communication from the surgeon 350. The controller 320 may record the surgical notes by, for example, storing the text and/or voice communication data in the memory device 336 and/or the removable memory device 340. If the controller 320 determines that the surgeon 350 has not requested the recording of surgical notes in process step 432 or after the surgical notes have been recorded in process step 434, the algorithm 400 advances to process step 440 described below.

In process step 436, the controller 320 determines if the surgeon 350 has requested that selection data be recorded. The surgeon 350 may request the recording of selection data by, for example, selecting an appropriate button on the touch-screen of the display device 346 or providing a recognized voice command via the microphone 342. If so, the controller 320 records the selections made by the surgeon 350 during the performance of the orthopaedic surgical procedure and/or screenshots of the images displayed to the surgeon 350 during the procedure. The controller 320 may record the selections and/or screenshots by, for example, storing the data indicative of the selections and images of the screenshots in the memory device 336 and/or the removable memory device 340. If the controller 320 determines that the surgeon 350 has not requested the recording of selection data in process step 436 or after the surgical notes have been recorded in process step 438, the algorithm 400 advances to process step 440.

Referring now to process step 440, the controller 320 determines if the current surgical procedure step has been completed. If the current surgical procedure step has not been completed, the algorithm 400 loops back to process step 418 wherein the navigational data is updated. The surgeon 350 may indicate that the surgical procedure step has been completed by selecting an appropriate button (e.g., a "NEXT" button) displayed on the display device 346. Additionally, if the surgeon 350 so decides, the surgeon 350 may skip the current surgical procedure step by simply clicking the appropriate button while not performing the surgical procedure step on the patient 430. In such a case, the controller 320 may be configured to detect this deviation from the workflow plan in process step 428 (i.e., detect that the surgeon 450 skipped the current surgical procedure step) by, for example, monitoring the use or lack thereof of the relevant medical device (e.g., surgical tool, orthopaedic implant, etc.).

If the current surgical procedure step has been completed, the algorithm 400 advances to process step 442. In process step 442, the controller 320 determines if the current surgical procedure step was the last surgical procedure step of the workflow plan determined in process step 412. If not, the algorithm 400 loops back to the process step 416 wherein the next surgical procedure step of the workflow plan is displayed to the surgeon 350. However, if the current surgical procedure step was the last surgical procedure step of the workflow plan, the algorithm 400 advances to process step 444 wherein surgical data may be stored for later retrieval. The surgical data may include any type of data generated prior to or during the performance of the orthopaedic surgical procedure. For example, the surgical data stored in process step 444 may include patient-related data, preoperative data, the deviation data recorded in process step 428, the surgical notes data recorded in the process step 434, and/or the selection data and screenshots stored in the process step 438. The surgical data may be stored on the hospital network 302 in, for example, the database 308. In this way, surgical data may be temporarily stored on the controller 320 in the memory device 336, the removable memory storage device 340, a hard drive, or other data storage device coupled with or included in the controller 320 and subsequently uploaded to the hospital network 302 for permanent and/or archival storage. The surgical data may be automatically stored in process step 444 (e.g., the controller 320 may be configured to automatically store the data in the database 308 upon completion of the orthopaedic surgical procedure) or the surgical data may be stored only upon authorization by the surgeon 350. Additionally, in some embodiments, the controller 320 may be configured to allow the surgeon 350 to review the surgical data and determine which surgical data is uploaded to the network 302.

The surgical data stored in the hospital network database 308 may be retrieved at a later time for review. For example, the surgical data may be reviewed by hospital staff to ensure compliance with hospital practices, reviewed by the surgeon 350 before check-up appointments of the patient 330, reviewed by interns or students for educational purposes, or the like. In some embodiments, the stored surgical data may be downloaded from the hospital network 302 to the remote information management system 304 via the communication link 312. For example, the surgeon 350 may download the surgical data to a remote computer located in the surgeon's 350 office. Additionally, the surgeon 350 may supplement the surgical data with additional surgical notes, diagrams, or comments by uploading such data from the system 304 to the network 302 for storage in, for example, the database 308. The uploaded data may be stored in relation to the stored surgical notes such that the uploaded data becomes a permanent or linked portion of the surgical data.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A computer assisted orthopaedic surgery system comprising:
   a surgical instrument configured to be positioned in a patient's knee joint,
   a processor, a memory device electrically coupled to the processor, and a display device having a display screen, wherein the memory device has stored thereon a plurality of instructions for facilitating a computer assisted orthopaedic surgery on the patient's knee joint, wherein the plurality of instructions, when executed by the processor, cause the processor to (i) determine a deviation from a surgical workflow plan for the computer assisted orthopaedic surgery based on one or more electronic signals generated by the surgical instrument and (ii) display on the display screen:

a) an image of the patient's tibia;

b) a first visual indicia on the image of an actual tibial resection surface, and c) a second visual indicia on the image of a planned tibial resection, wherein the first and second visual indicia are displayed together on the image.

2. The computer assisted orthopaedic surgery system of claim 1, wherein the plurality of instructions further cause the processor to display on the display screen a visual indicia of a comparison of the actual tibial resection surface to the planned tibial resection surface.

3. The computer assisted orthopaedic surgery system of claim 1, wherein the first visual indicia on the image represents an actual tibial resection plane, and the second indicia on the image represents a planned tibial resection plane.

4. The computer assisted orthopaedic surgery system of claim 1, wherein the surgical instrument comprises an array of sensors configured to perform measurements related to the patient's tibia.

5. The computer assisted orthopaedic surgery system of claim 1, wherein the plurality of instructions further cause the processor to display a plurality of pre-planned target surgical parameters and a plurality of actual surgical parameters corresponding to the pre-planned target surgical parameters.

6. The computer assisted orthopaedic surgery system of claim 1, wherein the actual tibial resection surface is at a greater depth than the planned tibial resection surface.

7. A computer assisted orthopaedic surgery system, comprising:

a computer, a display device having a display screen, a first array of sensors configured to be coupled to a patient bone, a second array of sensors configured to register points of the patient bone, the first array of sensors and the second array of sensors configured to cooperate with the computer to generate customized visual information, and wherein the display screen is configured to display the customized visual information, the customized visual information including a first graphical resection guide representing an actual resection surface, a second graphical resection guide representing a planned resection surface, and deviation data generated from one or more electronic signals received from the first array of sensors, the second array of sensors, or both the first and second arrays of sensors.

8. The system of claim 7, wherein the first graphical resection guide represents an actual resection plane, and wherein the second graphical resection guide represents a planned resection plane.

9. The system of claim 7, wherein the customized visual information is configured to display the actual resection surface at a greater depth than the planned resection surface.

* * * * *